US010265705B2

(12) United States Patent
Wong et al.

(10) Patent No.: US 10,265,705 B2
(45) Date of Patent: Apr. 23, 2019

(54) APPARATUS FOR MEASUREMENT OF SPINNING FORCES RELATING TO MOLECULES

(71) Applicant: President and Fellows of Harvard College, Cambridge, MA (US)

(72) Inventors: Wesley Philip Wong, Cambridge, MA (US); Kenneth Anders Halvorsen, Glenmont, NY (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/141,692

(22) Filed: Apr. 28, 2016

(65) Prior Publication Data

US 2016/0243560 A1 Aug. 25, 2016

Related U.S. Application Data

(63) Continuation of application No. 13/701,042, filed as application No. PCT/US2011/038716 on Jun. 1, 2011, now Pat. No. 9,354,189.
(Continued)

(51) Int. Cl.
*B04B 15/00* (2006.01)
*G01N 33/543* (2006.01)
(Continued)

(52) U.S. Cl.
CPC ......... *B04B 15/00* (2013.01); *G01N 15/1463* (2013.01); *G01N 21/17* (2013.01);
(Continued)

(58) Field of Classification Search
CPC .. G01N 21/07; G01N 21/6458; G02B 21/362; B04B 15/00; B04B 2013/006
See application file for complete search history.

(56) References Cited

U.S. PATENT DOCUMENTS 3,009,388 A 11/1961 Polanyi
3,727,066 A 4/1973 Louderback et al.
(Continued)

FOREIGN PATENT DOCUMENTS

EP 0 123 178 A2 10/1984
EP 0 589 556 A2 3/1994
(Continued)

OTHER PUBLICATIONS

European Examination Report for European Application No. EP 11728725.0 dated Jun. 16, 2016.
(Continued)

*Primary Examiner* — Timothy C Cleveland
(74) *Attorney, Agent, or Firm* — Wolf, Greenfield & Sacks, P.C.

(57) ABSTRACT

An apparatus for measuring a characteristic of a sample includes a sample measurement apparatus (1404), which includes a light source (1406) configured to illuminate the sample; and a detector (1412) configured to receive light from the sample. The sample measurement apparatus is sized and dimensioned to fit within a centrifuge receptacle, the centrifuge receptacle (1416) coupled to a spindle configured to rotate the centrifuge receptacle to apply a force to the sample.

23 Claims, 16 Drawing Sheets

Related U.S. Application Data

(60) Provisional application No. 61/350,088, filed on Jun. 1, 2010.

(51) Int. Cl.
    *G01N 21/17*     (2006.01)
    *G01N 15/14*     (2006.01)
    *G06T 7/20*     (2017.01)
    *G01N 11/00*     (2006.01)
    *G01N 15/00*     (2006.01)

(52) U.S. Cl.
    CPC . *G01N 33/54313* (2013.01); *G01N 33/54373* (2013.01); *G06T 7/20* (2013.01); *G01N 11/00* (2013.01); *G01N 2015/0065* (2013.01); *G01N 2203/0089* (2013.01)

(56) References Cited

U.S. PATENT DOCUMENTS

| | | | |
|---|---|---|---|
| 4,032,066 | A | 6/1977 | Wright |
| 5,712,710 | A | 1/1998 | Karakus et al. |
| 5,958,703 | A | 9/1999 | Dower et al. |
| 6,001,310 | A | 12/1999 | Shaffer et al. |
| 6,143,183 | A | 11/2000 | Wardwell et al. |
| 6,201,639 | B1 | 3/2001 | Overbeck |
| 6,654,102 | B1 | 11/2003 | Modares et al. |
| 7,052,650 | B2 | 5/2006 | Strick et al. |
| 8,491,454 | B2 | 7/2013 | Wong et al. |
| 8,795,143 | B2 | 8/2014 | Wong et al. |
| 9,354,189 | B2 | 5/2016 | Wong et al. |
| 9,897,597 | B2 | 2/2018 | Shih et al. |
| 2002/0177144 | A1 | 11/2002 | Remacle et al. |
| 2003/0077839 | A1 | 4/2003 | Takei |
| 2003/0155527 | A1* | 8/2003 | Natori ............... G01N 21/6458 250/458.1 |
| 2003/0166262 | A1 | 9/2003 | Strick et al. |
| 2004/0017567 | A1 | 1/2004 | Loicht et al. |
| 2005/0194325 | A1 | 9/2005 | Moore et al. |
| 2007/0155017 | A1 | 7/2007 | Wyatt |
| 2007/0231796 | A1 | 10/2007 | Majda |
| 2007/0238598 | A1 | 10/2007 | Kim et al. |
| 2009/0118140 | A1 | 5/2009 | Suzara |
| 2010/0137120 | A1 | 6/2010 | Wong et al. |
| 2012/0058008 | A1 | 3/2012 | Corbett et al. |
| 2012/0149129 | A1 | 6/2012 | Pai et al. |
| 2012/0238738 | A1 | 9/2012 | Hendrickson |
| 2013/0123089 | A1 | 5/2013 | Johns et al. |
| 2013/0130884 | A1 | 5/2013 | Wong et al. |
| 2013/0225219 | A1 | 8/2013 | Curry |
| 2013/0288349 | A1 | 10/2013 | Wong et al. |
| 2017/0045506 | A1 | 2/2017 | Shih et al. |

FOREIGN PATENT DOCUMENTS

| | | |
|---|---|---|
| JP | 11258081 A | 9/1999 |
| WO | WO 2008/112980 A2 | 9/2008 |
| WO | WO 2010/065477 A2 | 6/2010 |
| WO | WO 2011/153211 A1 | 12/2011 |
| WO | WO 2013/059044 A1 | 4/2013 |
| WO | WO 2015/166399 A1 | 11/2015 |

OTHER PUBLICATIONS

International Search Report and Written Opinion for Application No. PCT/US2009/066154 dated Jul. 27, 2010.
International Preliminary Report on Patentability for Application No. PCT/US2009/066154 dated Jun. 16, 2011.
International Search Report and Written Opinion for Application No. PCT/US2011/038716 dated Aug. 29, 2011.
International Preliminary Report on Patentability for Application No. PCT/US2011/038716 dated Dec. 4, 2012.
Bitar et al., Tarsal morphology and attachment ability of the codling moth *Cydia pomonella* L. (Lepidoptera, Tortricidae) to smooth surfaces. J Insect Physiol. Nov. 2009;55(11):1029-38. Epub Aug. 5, 2009.
Block et al., Bead movement by single kinesin molecules studied with optical tweezers. Nature. Nov. 22, 1990;348(6299):348-52.
Bustamante et al., Ten years of tension: single-molecule DNA mechanics. Nature. Jan. 23, 2003;421(6921):423-7.
Chon et al., A von Willebrand factor-derived heparin-binding peptide regulates cell-substrate adhesive strength and chemokinesis behavior. Biochim Biophys Acta. Jan. 30, 2002;1542(1-3):195-208.
Evans et al., Chemically distinct transition states govern rapid dissociation of single L-selectin bonds under force. Proc Natl Acad Sci U S A. Mar. 27, 2001;98(7):3784-9. Epub Mar. 13, 2001.
Evans et al., Dynamic strength of molecular adhesion bonds. Biophys J. Apr. 1997;72(4):1541-55.
Federle et al., Attachment forces of ants measured with a centrifuge: better 'wax-runners' have a poorer attachment to a smooth surface. J Exp Biol. Feb. 2000;203(Pt 3):505-12.
Fernandez et al., Force-clamp spectroscopy monitors the folding trajectory of a single protein. Science. Mar. 12, 2004;303(5664):1674-8.
Friedrich et al., The slow rotating centrifuge microscope NIZEMI—a versatile instrument for terrestrial hypergravity and space microgravity research in biology and materials science. J Biotechnol. Jun. 27, 1996;47(2-3):225-38.
Giessibl, Advances in atomic force microscopy. Rev Mod Phys. Jul. 29, 2003;75(3):949-83.
Grier, A revolution in optical manipulation. Nature. Aug. 14, 2003;424(6950):810-6.
Ha, Single-molecule fluorescence resonance energy transfer. Methods. Sep. 2001;25(1):78-86.
Halvorsen J. et al., Massively parallel single-molecule manipulation using centrifugal force. Biophys J. Jun. 2, 2010;98(11):L53-5.
Harvey et al., A microscope-centrifuge. Science. Jul. 11, 1930;72(1854):42-4.
Heinrich et al., Imaging biomolecular interactions by fast three-dimensional tracking of laser-confined carrier particles. Langmuir. Feb. 19, 2008;24(4):1194-203. Epub Jan. 17, 2008.
Hummer et al., Free energy surfaces from single-molecule force spectroscopy. Acc Chem Res. Jul. 2005;38(7):504-13.
Kellermayer et al., Folding-unfolding transitions in single titin molecules characterized with laser tweezers. Science.May 16, 1997;276(5315):1112-6.
Koo et al., Co-regulation of cell adhesion by nanoscale RGD organization and mechanical stimulus. J Cell Sci. Apr. 1, 2002;115(Pt 7):1423-33.
McClay et al., Intercellular recognition: quantitation of initial binding events. Proc Natl Acad Sci U S A. Aug. 1981;78(8):4975-9.
Mehta et al., Myosin-V is a processive actin-based motor. Nature. Aug. 5, 1999;400(6744):590-3.
Merkel et al., Energy landscapes of receptor-ligand bonds explored with dynamic force spectroscopy. Nature. Jan. 7, 1999;397(6714):50-3.
Monroe, The optical trap. Scientist. Aug. 29, 2005;19(16):48-52. Retrieved from the internet http://www.the-scientist.com/?articles. view/articleNo/16665/title/The-Optical-Trap/ on Jan. 28, 2013.
Neuman et al., Optical trapping. Rev Sci Instrum. Sep. 2004;75(9):2787-809.
Neuman et al., Single-molecule force spectroscopy: optical tweezers, magnetic tweezers and atomic force microscopy. Nat Methods. Jun. 2008;5(6):491-505.
Ribeck et al., Multiplexed single-molecule measurements with magnetic tweezers. Rev Sci Instrum. Sep. 2008;79(9):094301.
Rief et al., Reversible unfolding of individual titin immunoglobulin domains by AFM. Science. May 16, 1997;276(5315):1109-12.
Rief et al., Single molecule force spectroscopy of spectrin repeats: low unfolding forces in helix bundles. J Mol Biol. Feb. 19, 1999;286(2):553-61.
Salazar-Banda et al., Determination of the adhesion force between particles and a flat surface, using centrifuge technique. Powder Technology. Apr. 2007;173(2):107-17.

(56) References Cited

OTHER PUBLICATIONS

Tarsa et al., Detecting force-induced molecular transitions with fluorescence resonant energy transfer. Angew Chem Int Ed Engl. 2007;46(12):1999-2001.
Van Oijen et al., Single-molecule kinetics of lambda exonuclease reveal base dependence and dynamic disorder. Science. Aug. 29, 2003;301(5637):1235-8.
Vargas et al., A centrifuge for studies of fluid dynamics phenomena in a rotating frame of reference. Revista Mexicana de Fisica. Jun. 2002;48(3):255-266.
Wong, Exploring single-molecule interactions through 3D optical trapping and tracking: from thermal noise to protein refolding. PhD Thesis. Harvard University. Cambridge, Massachusetts. Oct. 2006.
Woodside et al., Nanomechanical measurements of the sequence-dependent folding landscapes of single nucleic acid hairpins. Proc Natl Acad Sci U S A. Apr. 18, 2006;103(16):6190-5. Epub Apr. 10, 2006.
Invitation to Pay Additional Fees dated Aug. 13, 2015 for PCT/US2015/027290.
International Search Report and Written Opinion dated Oct. 28, 2015 for PCT/US2015/027290.
International Preliminary Report on Patentability dated Nov. 3, 2016 for PCT/US2015/027290.
Extended European Search Report dated Nov. 10, 2017 for Application No. EP 15783027.4.
International Search Report and Written Opinion dated Apr. 12, 2017 in connection with International Application No. PCT/US2016/065341.
International Preliminary Report on Patentability dated Jun. 21, 2018 in connection with International Application No. PCT/US2016/065341.
International Search Report and Written Opinion dated Jun. 7, 2017 in connection with International Application No. PCT/US2017/019318.
Ackbarow et al., Strength and robustness of protein materials. Encyclopedia of Nanoscience and Nanotechnology. 2011;23:349-87.
Basle et al., Protein chemical modification on endogenous amino acids. Chem Biol. Mar. 26, 2010;17(3):213-27. doi: 10.1016/j.chembiol.2010.02.008.
Claridge et al., Electrons, photons, and force: quantitative single-molecule measurements form physics to biology. ACS Nano. Feb. 22, 2011;5(2):693-729.
De Vlaminck et al., Magnetic forces and DNA mechanics in multiplexed magnetic tweezers. PLoS One. 2012;7(8):e41432. Epub Aug. 3, 2012.
Dessinges et al. Stretching single stranded DNA, a model polyelectrolyte. Phys Rev Lett. Dec. 9, 2002;89(24):248102(1-4), Epub Nov. 22, 2002.
Douglas et al. Self-assembly of DNA into nanoscale three-dimensional shapes. Nature 459, 414-418 (2009).
Kim et al., A high-resolution magnetic tweezer for single-molecule measurements. Nucleic Acids Res. Nov. 2009;37(20):e136. doi: 10.1093/nar/gkp725. Epub Sep. 3, 2009.
Koirala et al., Single-molecule mechanochemical sensing using DNA origami nanostructures. Angew Chem Int Ed Engl. Jul. 28, 2014;53(31):8137-41. doi: 10.1002/anie.201404043. Epub Jun. 16, 2014.
Koussa et al., DNA nanoswitches: a quantitative platform for gel-based biomolecular interaction analysis. Nat. Methods. Feb. 1, 2015;12(2):123-6. Suppl Protocol, 4 pages. Epub Dec. 8, 2014.
Koussa et al., Protocol for sortase-mediated construction of DNA-protein hybrids and functional nanostructures. Methods. May 15, 2014;67(2):134-41. doi: 10.1016/j.ymeth.2014.02.020. Epub Feb. 22, 2014.
Lansdorp et al., A high-speed magnetic tweezer beyond 10,000 frames per second. Rev Sci Instrum. Apr. 2013;84(4):044301(1-5), doi:10.1063/1.4802678.
Otto et al., Real-time particle tracking at 10,000 fps using optical fiber illumination Opt. Express. Oct. 25, 2010;18(22):22722-33, doi: 10.1364/OE.18.022722.
Pfitzner et al., Rigid DNA beams for high-resolution single-molecule mechanics. Angew Chem Int Ed Engl. Jul. 22, 2013;52(30):7766-71. doi: 10.1002/anie.201302727. Epub Jun. 21, 2013.
Pinheiro et al., Challenges and opportunities for structural DNA nanotechnology. Nat Nanotechnol. Dec. 2011;6:763-72.
Plesa et al., Ionic permeability and mechanical properties of DNA origami nanoplates on solid-state nanopores. ACS Nano. Jan. 28, 2014;8(1):35-43, doi: 10.1021/nn405045x., Epub Dec. 5, 2013.
Robison et al., High-throughput single-molecule studies of protein-DNA interactions. FEBS Lett. Oct. 1, 2014;588(19):3539-46. Epub May 21, 2014.
Schmied et al., DNA origami-based standards for quantitative fluorescence microscopy. Nat. Protocols 9, 1367-1391 (2014).
Sitters et al. Acoustic force spectroscopy. Nature Methods 12, 47-50 (2015).
Wagenbauer et al., Quantifying quality in DNA self-assembly. Nat Commun. Apr. 22, 2014; 5:3691, doi: 10.1038/ncomms4691, 7 pages.
Wong et al., Exploring reaction pathways of single-molecule interactions through the manipulation and tracking of a potential-confined microsphere in three dimensions. Mat Res Soc Symp Proc. 2004. vol. 790: P5.1.1-5.1.12, Cambridge Univ. Press, Symposium held Dec. 1-4, 2003, Boston, MA, USA.
Wong et al., The effect of integration time on fluctuation measurements: calibrating an optical trap in the presence of motion blur. Optics Express. Dec. 11, 2006;14(25):12517-31.
Yurke et al., Using DNA to power nanostructures. Genetic Programming and Evolvable Machines. 2003;4:111-22.
Zhang et al., Control of DNA strand displacement kinetics using toehold exchange. J Am Chem Soc. 2009;131(47):17303-14.
Zhang et al., Optimizing the specificity of nucleic acid hybridization. Nat Chem 4, 208-214 (2012).

* cited by examiner

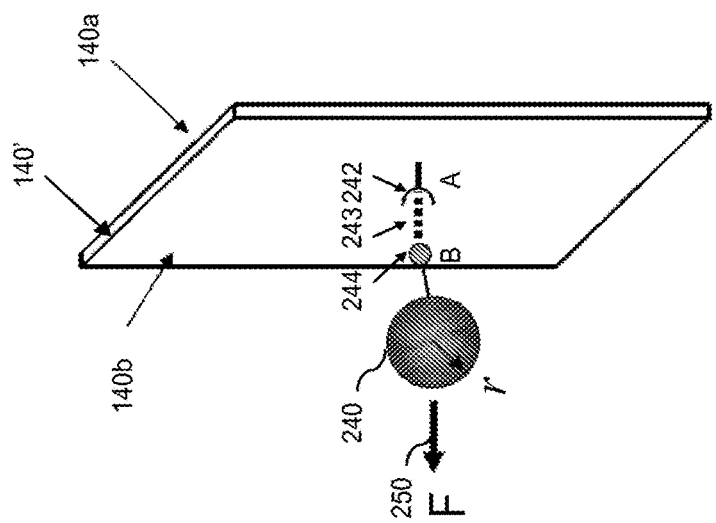
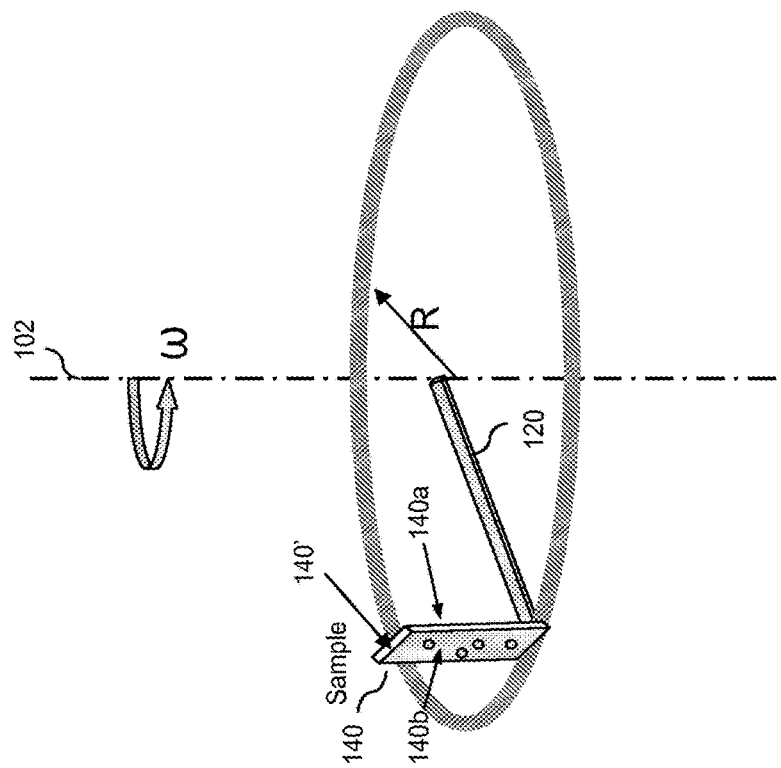
FIG. 2B
FIG. 2A

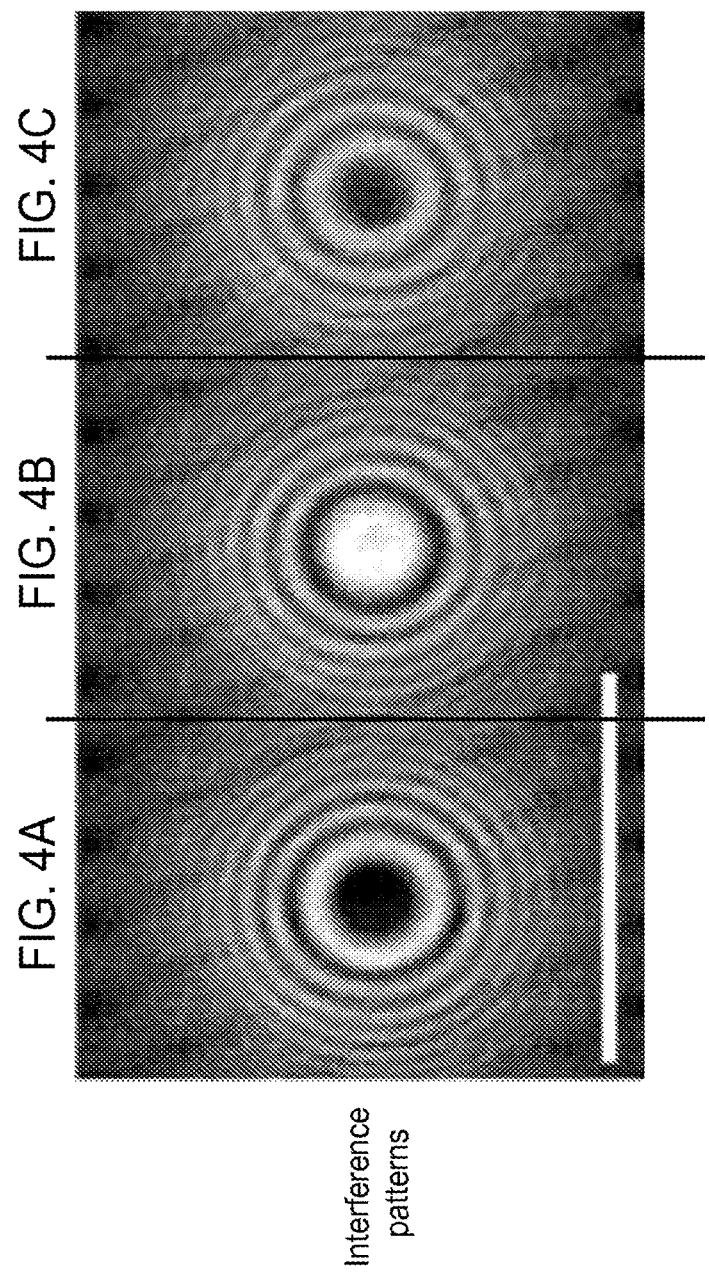

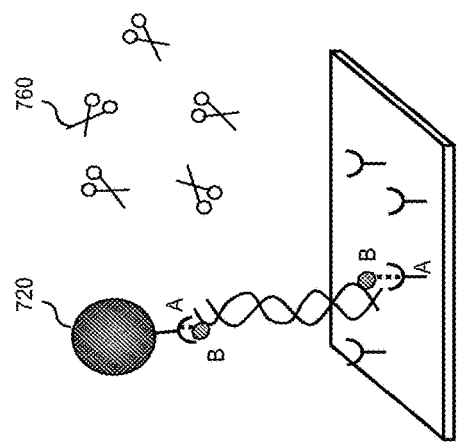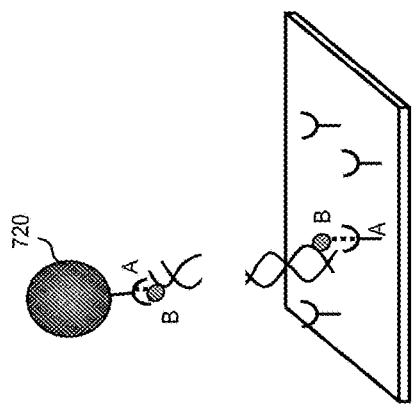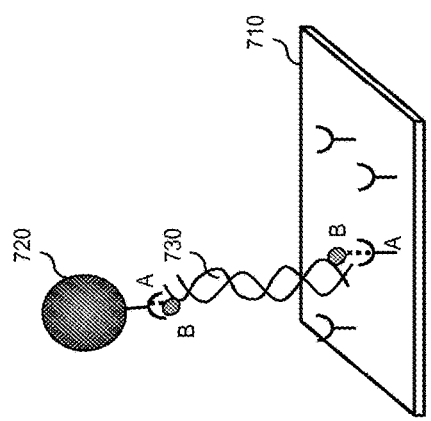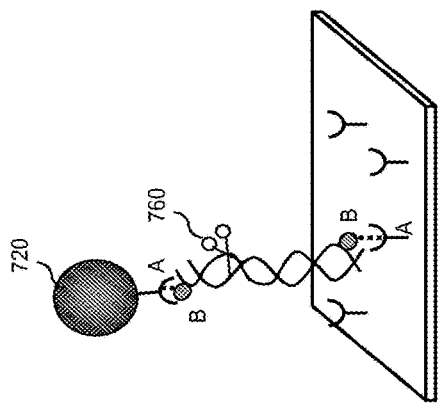

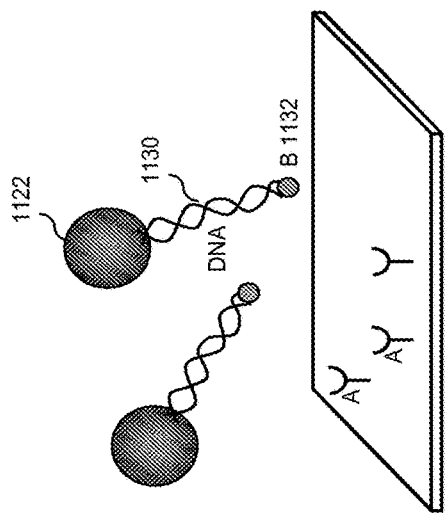
FIG. 11A
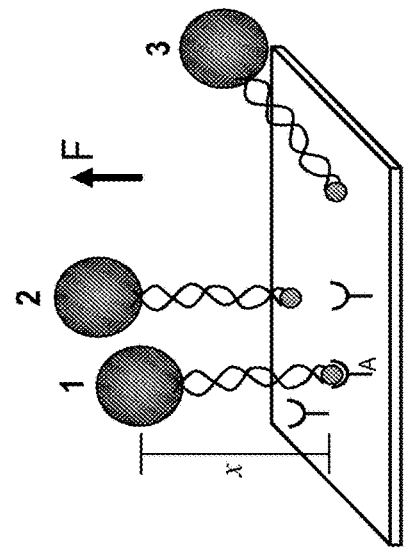
FIG. 11B
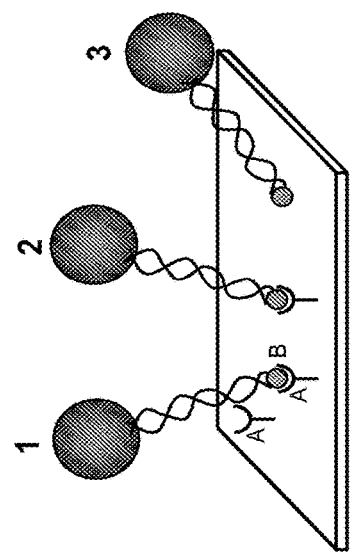
FIG. 11C
FIG. 11D

APPARATUS FOR MEASUREMENT OF SPINNING FORCES RELATING TO MOLECULES

CROSS-REFERENCE TO RELATED APPLICATIONS

This application is a continuation of U.S. patent application Ser. No. 13/701,042, filed Jan. 30, 2013, which is a national stage filing under 35 U.S.C. § 371 of International Application No. PCT/US2011/038716 filed Jun. 1, 2011, which claims the benefit under 35 U.S.C. § 119(e) of U.S. Provisional Application Serial No. 61/350,088, filed Jun. 1, 2010, the entire contents of each of which are incorporated herein by reference.

This application is related to U.S. application Ser. No. 12/326,279, filed Dec. 2, 2008, and entitled "Spinning Force Apparatus," the contents of which are incorporated herein by reference.

BACKGROUND

This invention relates to measurement of forces relating to molecules.

The ability to quantify interactions between biomolecules is of great interest for scientific and medical research, as well as for drug development. Examples of measurable characteristics of a biomolecular interaction include the affinity (e.g., how strongly the molecules bind/interact) and the kinetics (e.g., rates at which the association and dissociation of molecules occur) of the interaction. Traditionally, such characteristics are measured in solution, using methods such as calorimetry, stop-flow imaging, or surface plasmon resonance. These bulk measurements are limited in many ways, including 1) they report only average behavior and thus may lose important details associated with metastable states and rare events, and 2) they measure chemistry in the absence of externally applied mechanical stress, which can be dramatically different from crowded and dynamic environments in living systems.

Recent development in single molecule measurement methods offers a different approach in quantifying molecular interactions by examining the behavior of individual molecules rather than measuring the properties of bulk solutions. This approach enables the observation of rare or fleeting events that can be obscured by ensemble averaging. The resulting detailed information of molecular transitions helps researchers to identify metastable states and to study the transitions rates and the chemical pathways between such states. Furthermore, heterogeneities between molecules in a population and within the behavior of a single molecule can both be quantified.

Currently, force probes that apply single molecule measurement methods include atomic force microscopes (AFM), optical traps, magnetic tweezers, biomembrane force probes, and flow chambers. Despite many advantages, these devices still have several limitations. For example, due to technical complexities, some systems require a large investment of money and time (e.g. optical trap systems typically cost $150k or more). Additionally, molecular interactions are studied one molecule at a time in most cases. Statistical characterization of these interactions is therefore slow and painstaking, requiring hundreds or thousands of measurements which are typically performed in a serial manner.

SUMMARY

In a general aspect, an apparatus for measuring a characteristic of a sample includes a sample measurement apparatus, which includes a light source configured to illuminate the sample; and a detector configured to receive light from the sample. The sample measurement apparatus is sized and dimensioned to fit within a centrifuge receptacle, the centrifuge receptacle coupled to a spindle configured to rotate the centrifuge receptacle to apply a force to the sample.

Embodiments may include one or more of the following.

The sample measurement apparatus further comprises a lens configured to receive light from the sample, and wherein the detector is configured to receive light from the lens. The lens includes an aspheric lens. The sample measurement apparatus includes only one lens.

The apparatus further includes the centrifuge receptacle. The apparatus further includes a base disposed within the centrifuge receptacle and configured to received the sample measurement apparatus. The centrifuge receptacle includes at least one of a centrifuge tube, a swing bucket, and a rotor. The centrifuge receptacle is a centrifuge tube having a volume of less than or equal to about 50 mL.

The sample measurement apparatus further includes a lens tube, wherein the light source, the lens, and the detector are disposed within the lens tube. The apparatus further includes a battery coupled to the centrifuge receptacle and electrically connected to the light source and the detector. The battery is disposed within the centrifuge receptacle.

The apparatus further includes a recording device coupled to the centrifuge receptacle, the recording medium configured to record a signal received from the detector. The recording device is disposed within the centrifuge receptacle.

The apparatus further includes a wireless communications module configured to wirelessly transmit a signal received from the detector. The apparatus further includes a computing device electrically connected to the detector. The computing device is external to the centrifuge receptacle. The detector is electrically connected to the computing device via a rotary joint.

The apparatus further includes a computing device external to the centrifuge receptacle. The detector is optically connected to the computing device via a fiber optic rotary joint.

The spindle forms part of a centrifuge. An optical axis of the sample measurement apparatus is substantially perpendicular to an axis of rotation of the centrifuge receptacle.

Among other advantages and features, the spinning force system and methods described herein can provide one or more of the following advantages.

A small-scale spinning force system uses a benchtop centrifuge, which is standard equipment in many scientific laboratories. The use of standard equipment decreases the cost and increases the accessibility of the spinning force approach to molecular characterization. Furthermore, the components of the small-scale spinning force system are themselves relatively inexpensive.

The system and methods of operation can provide massively-parallel high-throughput single-molecule force measurements at a low cost. More specifically, rotation-induced forces (e.g., centrifugal forces and viscous drag forces) can be used to manipulate single molecules (e.g., proteins or DNAs) or molecular complexes (e.g., receptor-ligand protein pairs), enabling forces to be applied simultaneously to many subjects. Each subject can be observed directly and independently for true single-molecule detection. The efficiency of experiments can be improved, reducing the time to conduct an experiment from days to minutes. More than simply speeding up experiments, this efficiency also enables new experiments such as near equilibrium measurements that observe interactions with hour-long lifetimes, which would be unfeasible with sequentially collected statistics. Furthermore, with larger statistical sets more easily attainable, more detailed characterizations, model testing, and observations of population heterogeneity are possible. Parallel measurements can also be used to test families of interactions simultaneously (e.g., multiple drug candidates could be tested simultaneously against a target receptor).

The system and methods of operation can provide accurate force control in a wide range of directions and magnitudes. Through force control, the system and methods of operation can be used to quantify force dependent interactions, including measuring the force dependence of kinetic parameters (e.g., $K_{on}$ and $K_{off}$) and molecular subtleties which would be invisible from population averaging. Using this system, the mechanical properties of biomolecular complexes (e.g., compliances of DNAs and proteins) and cellular targets (e.g., elasticity of stress-bearing cells) can be studied, yielding valuable information into both the structure and the function of those subjects.

The centrifugal force field applied to a sample in the system and methods of operation describe herein is macroscopically uniform, stable without the need for active feedback, calibration-free, and dynamically controllable in an essentially deterministic way. Thus, a desired force history can be applied to an ensemble of single molecules without the need for active feedback. The force field conveniently couples to mass density, eliminating the possibility of radiative damage and expanding the range of systems that can be studied with force (e.g., beads or objects made of any material can be used, as long as they have a different mass density than their surroundings). Furthermore, by varying the bead type, bead size, and rotation speed, a wide range of forces, at least from sub-femtoNewtons to nanoNewtons, can be achieved.

The system and methods of operation can be conveniently integrated with various types of force probes to generate forces in multiple dimensions with high flexibility. For example, the system can be used in conjunction with optical traps, magnetic tweezers and/or microfluidic devices to generate a combination of forces (such as gradient and scattering forces, magnetic forces, hydrodynamic forces, and centrifugal forces). Each force can be applied to a sample in a different direction, with a different magnitude, and/or at a different test stage.

The system and methods of operation can also be conveniently integrated with various imaging techniques to provide real-time observation with high temporal and spatial resolution. For example, using interference techniques and diffraction analysis, the position of individual particles in a sample can be ascertained with sub-nanometer accuracy. Also, fluorescent imaging enables visualization of subtle molecular transitions during experiment. Moreover, using video tracking by high-speed CCD cameras, molecular events can be detected on the scale of microseconds.

The systems and methods described herein are also more cost effective and simpler to use than other common methods of molecular spectroscopy. The material cost of a spinning force system is generally less than the cost of a typical laboratory microscope. Furthermore, experiments using this system are straightforward, with a pre-preprogrammed force protocol, minimal setup, and little or no need for user intervention.

Other features and advantages of the invention are apparent from the following description and from the claims.

BRIEF DESCRIPTION OF DRAWINGS

FIG. 2A is a schematic representation of a sample coupled to the spinning force system of FIG. 1.

FIG. 2B shows a centrifugal force applied to the sample of FIG. 2A.

FIGS. 4A-4C show the interference patterns of a sample imaged by a reflection interference contrast microscope at three different heights, respectively.

FIGS. 7A-7D are schematic representations of a further procedure for preparing a sample to be measured by the spinning force system of FIG. 1.

FIGS. 11A-11D are schematic representations of a procedure for preparing a sample to be measured by the spinning force system of FIG. 1.

DETAILED DESCRIPTION

1 System Overview

Figure 1:
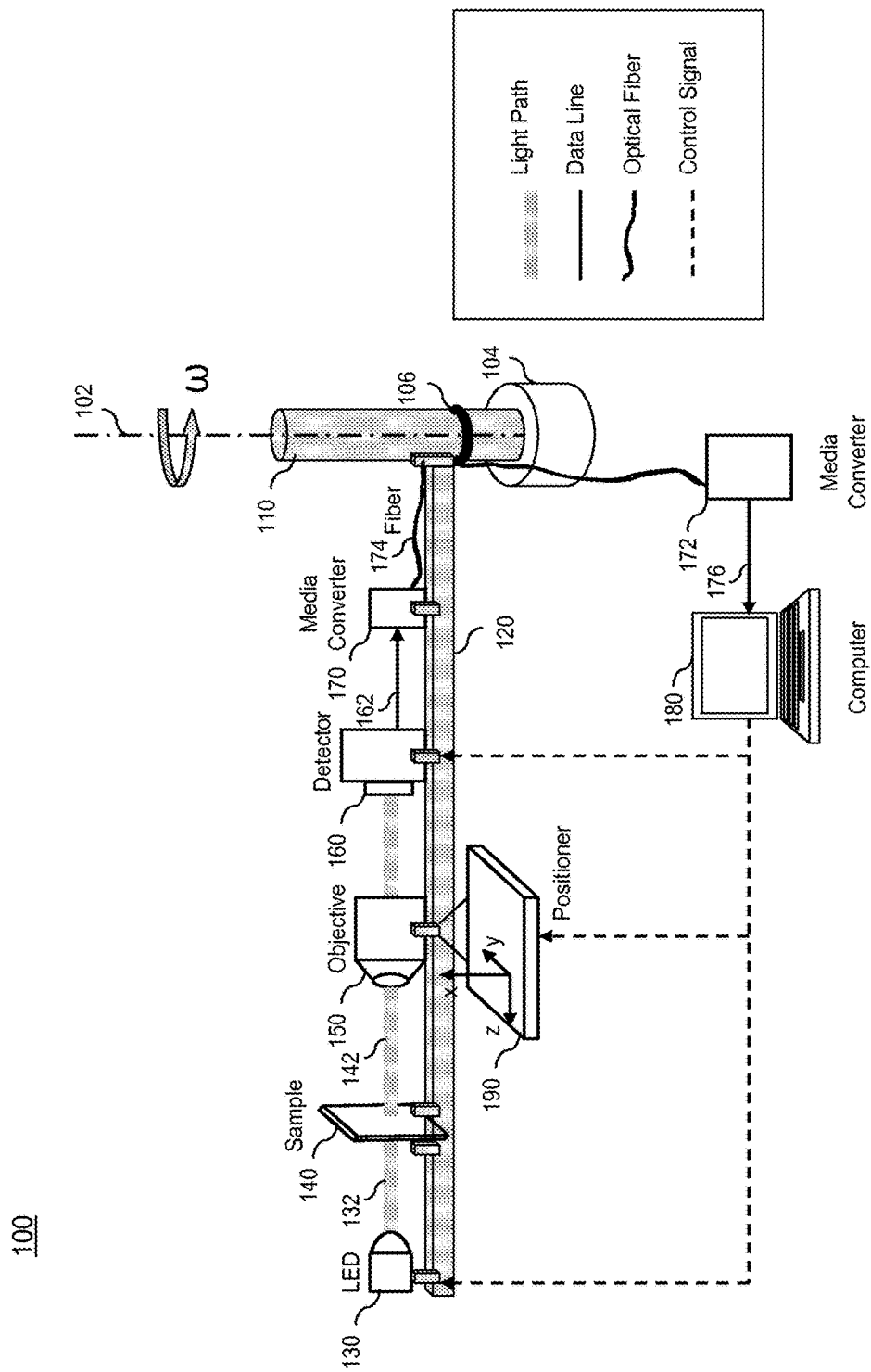
FIG. 1 is a schematic representation of one embodiment of a spinning force system.

Referring to FIG. 1, a spinning force system 100 includes a rotary arm 120 mechanically coupled to a rotary stage 110 (for instance, part numbers ADRT-150 and CP20, Soloist available from Aerotech (Pittsburgh, Pa.)) configured to rotate about a central axis 102 at an adjustable angular velocity ω. Rotary stage 110 is housed and supported on a stationary base 104 immobilized on a platform (not shown) such as a vibration-free optical table. The motion of rotary stage about central axis 102 is computer controlled.

Rotary arm 120 extends radially outward from central axis 102 to support a set of optical, mechanical, and electrical components for detecting characteristics (e.g., motion, optical, and geometric characteristics) of a sample 140 to be measured by system 100. These components include, for example, a light source 130, an objective 150, a light detector 160, and a media converter 170. In operation, these components are moved by rotary arm 120 to rotate about central axis 102 at the same angular velocity ω. Rotary arm 120 may also carry one or more positioning elements (e.g., adjustment screws for coarse adjustment, such as screw AJS100-02H available from Newport (Irvine, Calif.) and electromechanical stages such as piezoelectric positioners for fine adjustment, such as piezo AE0505D08F available from Thorlabs (Newton, N.J.)) for adjusting the position of each component coupled to arm 120. Examples of positioning elements will be described in greater detail below.

In this example, light source 130 is mounted at a distal end of rotary arm 120 for emitting a light beam 132 to illuminate a selected region of sample 140. Examples of light source 130 suitable for use in system 100 include various types of lamps (such as LED bulbs (e.g., LED lamp LED528E available from Thorlabs) and xenon arc lamps) and lasers (such as single- and multiple-wavelength lasers). Light source 130 may also include a set of optical components such as lenses, mirrors, and filters (not shown) for controlling the characteristics of its outgoing beam 132. For example, a condenser with diaphragms may be used for tuning the emission intensity of beam 132, and a color filter may be used for transmitting light at only selected wavelengths.

Sample 140 is mounted onto rotary arm 120 with a sample holder (not shown) fastened to the arm. Depending on the particular implementation, sample 140 may include an acrylic sample chamber (not shown) in which experiment subjects (such as cells, biomolecules, and DNA strands) are sealingly contained. The sample chamber may consist of two parallel cover glasses separated by a 1 mm o-ring, forming an enclosed volume that can be filled with buffer and beads. In some implementations, sample 140 is oriented such that the surfaces of the cover glasses are aligned in parallel to central axis 102. When rotary arm 120 rotates, the contents of sample 140 experience a centrifugal force normal to the cover glasses. In other implementations, sample 140 is oriented at a selected (and possibly adjustable) angle with respect to central axis 102, enabling the centrifugal force to be applied in any given direction.

Light beam 142 exiting sample 140 is received by objective 150 to produce a real image of the illuminated region of sample 140. The optical characteristics of objective 150 (e.g., magnification and numerical aperture) are selected depending on the particular implementation. For example, a 20×air-immersion objective may be used for applications that require a wide field of view, whereas a 100× oil-immersion objective may be preferred for applications that require a high spatial resolution.

Preferably, the relative position of objective 150 with respect to sample 140 is adjustable in three dimensions (x-, y- and z-directions shown in the figure), allowing images of different regions of the sample to be collected at various focal depths. In this example, objective 150 is staged on a piezoelectric positioner 190, which can be translated along each of the x-, y-, and z-directions by an external control signal (e.g., provided by a computer). In other examples, sample 140 (instead of objective 150) may be staged on positioner 190 for linear translation in those three dimensions.

Images formed by objective 150 are received by detector 160 and subsequently converted into electronic signals 162. One example of a detector suitable for use is a charge-coupled device (CCD), such as a 12-bit 5 megapixel CCD camera (e.g., part number GC 2450 available from Prosilica (Newburyport, Mass.)). Another example of a suitable detector is a CMOS detector. Preferably, detector 160 is capable of acquiring successive images at a speed sufficiently fast to enable video tracking of sample 140 at a high temporal resolution (e.g., 1 kHz). In some examples, light from objective 150 is first transformed through an intermediate optical system (not shown) before reaching detector 160. The intermediate optical system may include one or more elements such as lenses, filters, polarizers, and pinholes.

Electronic signals 162 from detector 160 are delivered, for example, using electrical, optical, or wireless transmission means, to be passed onto a computer 180. In this example, signals 162 are transmitted sequentially through an electronic-to-optical media converter 170, an optical fiber 174, and an optical-to-electronic media converter 172. Exemplary media converters are available from IMC Networks, Foothill Ranch, Calif. (part numbers 855-10734 and 855-10735). Both media converter 172 and computer 180 are positioned on a stationary platform (not shown). Using proper interfacing software, computer 180 decodes electronic signals 176 from media converter 172 to reproduce images of sample 140 on a screen. Optionally, optical fiber 174 is coupled to rotary stage 110 through a fiber optic rotary joint (not shown; e.g., part number MJX-155-28-SC available from Princetel, Pennington, N.J.), which can be further integrated into an electrical slipring 106 (e.g., part number SRF24 available from Princetel) of rotary stage 110. Power for detector 160, media converter 174, light source 130, and positioner 190 may be transmitted through slipring 106, allowing dynamic control of these components during rotation of system 100.

Computer 180 is used for viewing and processing images of sample 140. In addition, computer 180 is also configured to provide various control signals to control individual components of spinning force system 100. For example, computer 180 may be coupled to an electric motor (not shown) for controlling a rotational drive force to change the angular speed w of rotary stage 110. Computer 180 may also be coupled to a positioning device (not shown) for adjusting a distance between light source 130 and sample 140, or coupled to positioner 190 for translating objective 150 in each of x-, y-, and z-directions to select detection regions and to control focal depth. Computer 180 may also be configured to control the optical characteristics of light source 130 (e.g., the brightness and the frequency range of output beam 132) as well as the image acquisition variables of detector 160 (e.g., readout rate, integration time, and electronic gain). Additionally, computer 180 may provide control signals based on previously acquired data, enabling real-time feedback control.

2 Operation 2.1 Force Application

Referring to FIGS. 2A and 2B, when rotary arm 120 is in operation, sample 140 rotates at an angular velocity ω and at a distance R from the center of axis 102. For illustrative purposes, in this example, sample 140 includes a cover slip 140' having an inner surface 140a and an outer surface 140b with respect to axis 102. Both surfaces are aligned in parallel with axis 102. A particle 240 (e.g., a bead) adheres to outer surface 140b through a chemical bond 243 formed between molecule A 242 and molecule B 244. In this example, molecule A is a receptor chemically linked to outer surface 140b, and molecule B is a ligand chemically linked to particle 240. (The techniques and methods for forming such linkages will be described in greater detail below).

When particle 240 undergoes circular motion, a centripetal force F is exerted on the particle, as defined by the following equation:

$$F = \frac{mv^2}{R} \quad (1)$$

where F is the net centripetal force, m and v are the mass and the linear velocity of the particle, respectively, and R is the distance of the particle from rotation axis 102. In a rotating reference frame in which orbiting particle 240 appears stationary, particle 240 experiences an inertial centrifugal force equal to F in a direction perpendicular to outer surface 140b and away from central axis 102 (shown by arrow 250). In some examples where particle 240 is a spherical bead in solution with radius r and relative density ρ, rewriting equation (1) in terms of angular velocity ω yields:

$$F = \frac{4\pi\rho r^3 R\omega^2}{3} \quad (2)$$

When sample 140 rotates about axis 102 at a very low speed, centrifugal force F is countered by the interaction force of chemical bond 243, allowing particle 240 to continue to adhere to surface 140b. As the rotational speed ω rises, the increasing magnitude of centrifugal force F causes bead 240 to move with respect to surface 140b. The characteristics of the relative motion (e.g., the root-mean-square displacement or the direction of the motion) can be monitored and analyzed to quantify certain chemical and/or mechanical properties of bond 243 (e.g., properties associated with its transitional states and conformational changes). The increasing F may also cause the rupture of chemical bond 243, at which point, particle 240 is released from surface 140b. The magnitude of centrifugal force F at the particle release indicates the rupture force of chemical bond 243.

During operation, the magnitude of centrifugal force F can be controlled, for example, by adjusting the angular velocity ω of rotary arm 120. For instance, sample 140 can be subjected to multiple cycles of force application in which the centrifugal force on particle 240 is increased and/or decreased through step changes in angular velocity ω.

In addition to changing the angular velocity ω, it is also possible to change the radius of rotation R either statically or dynamically by changing the sample position relative to the axis of rotation. For example, in system 100, sample 140 may be mounted to an adjustable rotary arm with extendible length, or staged on a positioner that can be translated in a radial direction with respect to central axis 102.

In cases where particle 240 is a spherical bead, the centrifugal force F can also be varied by changing one or more of the particle characteristics ρ and r shown in equation (2). For example, microspheres are commercially available in a wide range of materials and sizes (see Table 1 below). By conjugating subjects of study (e.g., molecules or cells) to selected microspheres, the centrifugal force applied to the microspheres (and translated to the subject) can be varied based on bead properties. In addition, the degree of monodispersity of beads can control the range of forces applied for a given spin. For instance, a highly monodisperse sample (e.g., using beads of substantially the same size and properties) may cause all beads to experience the same force, while a polydisperse sample (e.g., using beads of various sizes and/or properties) would have a wide range of forces being applied. Moreover, ρ of particle 240 can also be altered by changing the density of the buffer solution. Furthermore, the geometry of the sample chamber can be varied to control the effects of fluid flow, which can add hydrodynamic forces to immobilized particles in the chamber.

TABLE 1

The materials and sizes of common beads

| Bead Material | Specific Density (g/cm³) | Size Range (μm) |
| --- | --- | --- |
| Borosilicate | 1.5 | 1-100+ |
| Polystyrene | 0.05 | 0.05-100+ |
| Silica | 1.2 | 0.01-100 |
| Gold | 18.3 | 0.002-0.25 |
| Melamine | 0.51 | 0.5-10 |
| Iron Oxide | 4.24 | 1-10 |

With proper parameter selection, the force applied to particle 240 can span 9 orders of magnitude, ranging from microNewtons (e.g., r=10 μm, ρ=1.5 g/cm³, R=500 mm, ω=100 Hz) to femtoNewtons (e.g., r=1 μm, ρ=0.05 g/cm³, R=250 mm, ω=2 Hz).

The direction of the centrifugal force F can also be controlled. In some examples, sample 140 may be configured in an orientation perpendicular to rotational axis 102, resulting in a centrifugal force F along surface 140b. In other examples, sample may be configured to form a selected angle with respect to rotational axis 102 so that centrifugal force F may be applied in any given direction. For instance, a compressive (rather than tensile) force can be applied to particle 240 if the particle is positioned on inner surface 140a (rather than outer surface 140b) of the cover glass. For particular implementations, it may be desirable to place sample in a parallel position with respect to rotation axis 102 because pulling particle 240 away from surface 140b reduces the likelihood of the particle forming new interactions with unoccupied binding sites of molecule A on the surface 140b.

In addition to centrifugal force F, other types of forces can also be applied to particle 240 through spinning For example, if particle 240 is contained in a chamber filled with a liquid medium, the rotation of sample 140 can generate regional flows that exert a viscous drag force D to particle 240. The direction of the drag force depends on factors such as the geometry of the chamber and the orientation of the sample. The magnitude of the drag force depends on factors such as the viscosity and the temperature of the liquid medium, the size of the particle, and the rotational velocity and acceleration of the sample.

2.2 Observing Motion Characteristics

In spinning force system 100, motion of particle 240 (e.g., displacement caused by molecular folding, unfolding or rupture of bond 243) can be observed by video tracking methods (e.g., by taking successive images of the particle at a high temporal resolution). Because light source 130, sample 140 and objective 150 rotate together at the same angular velocity ω, these three components appear stationary to each other in a rotating reference frame. Therefore, images of particle 240 can be formed using traditional imaging techniques, including transmitted- or reflected-light techniques and fluorescence techniques.

Figures 3A, 3B:
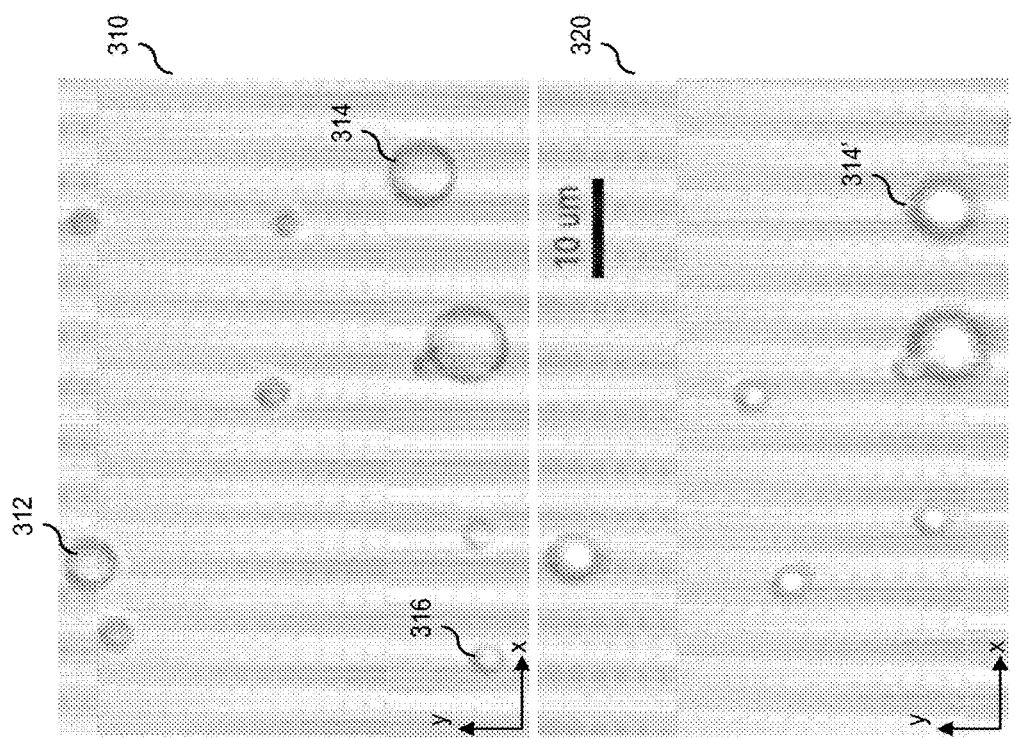
FIGS. 3A and 3B are transmitted light images of a sample generated at two different focal depths, respectively.

Referring to FIGS. 3A and 3B, images 310 and 320 are transmitted-light images of the same region of sample 140 produced at two different focal depths, respectively. In this example, sample 140 contains multiple beads (appearing, for example, as circular objects 312, 314 and 316 in image 310) near surface 140b. The location of each bead in the images represents the lateral position of the bead (e.g., along x- and y-axes of FIGS. 1, 3A and 3B). The image pattern of the bead (e.g., the size, the sharpness and the ring pattern of circular objects 312, 314 and 316) indicate the focal depth, namely, the distance of the bead from objective 150 (e.g., along z-axis of FIG. 1). This focal depth can be used to represent the relative position of the bead above surface 140b.

By analyzing the lateral position and the image pattern of individual beads, the movement of the beads with respect to time can be characterized in a three-dimensional space. Such characterization enables the quantification of the affinity and the kinetics of chemical bond 243 that links the bead to surface 140b. For example, before spinning, the position of objective 150 can be adjusted such that particle 240 situates in the objective's focal plane, resulting in a sharp in-focus image when the particle adheres to surface 140b. During spinning, if the centrifugal force F is sufficiently strong to cause bond rupture, particle 240 is quickly (typically at a speed of microns/s or faster) pulled away by centrifugal force F from surface 140b (e.g., along z-axis of FIG. 1). The escape of the particle from the objective's focal plane can be observed by changes in the characteristics of the detected image that are correlated with changes in focal depths. For example, a disappearance or blurriness of a circular pattern representing particle 240 (e.g., similar to the disappearance of object 316 from image 320 or the blurriness of object 314' in image 320) indicates that the particle is being pulled away from the focal plane of objective 150, e.g., as a result of bond rupture. Once bond rupture is identified, the bond force can be computed based on the magnitude of centrifugal force F, as defined in equation (1) or (2).

In examples where bond rupture is not necessarily observed or desired, detecting particle movement can provide valuable information about the compliance of a molecular tether that includes bond 243. For example, the displacement of particle 240 subjected to varying amplitude of centrifugal force F can be used to compute the elastic modulus of the molecular tether, and possibly to map the force dependency of such modulus. Also, stepwise changes in the position of particle 240 may indicate the transitions between molecular states that are associated with conformational changes of a chemical bond. For example, a bead that remains tethered but moves suddenly away from the cover glass can signify unfolding of a protein domain.

The transmitted light imaging technique described above can easily provide a spatial resolution along the optical axis of about 100 nm for observation. In certain implementations where a higher resolution is desirable, more sophisticated imaging and image processing techniques can also be applied. For example, by using advanced techniques such as using transmitted or reflected light interference patterns of individual beads, the position of a bead relative to surface 140b can be determined with sub-nanometer accuracy.

Referring to FIGS. 4A-4C, the interference patterns of a single particle imaged by a reflection interference contrast microscope (RICM) at three different heights are shown, respectively. In these figures, the alternation of dark and bright fringes as well as the intensity and the size of each fringe can be decoded to reconstruct the height profile of the particle with a sub-nanometer axial resolution. (The white bar shown in these figures represents 10 μm). An example of particle tracking using the RICM technique is described by Heinrich et al., in Fast Three-Dimensional Tracking of Laser-Confined Carrier Particles, published in *Langmuir*, 24(4):1194-1203, 2008, the contents of which are incorporated herein by reference.

In addition to the aforementioned imaging techniques, fluorescence techniques can also be implemented alone or together with transmitted/reflected light techniques to enhance resolution and to enable visualization of subtle molecular transitions during experiment.

3 Small-scale Spinning Force System

Figure 14:
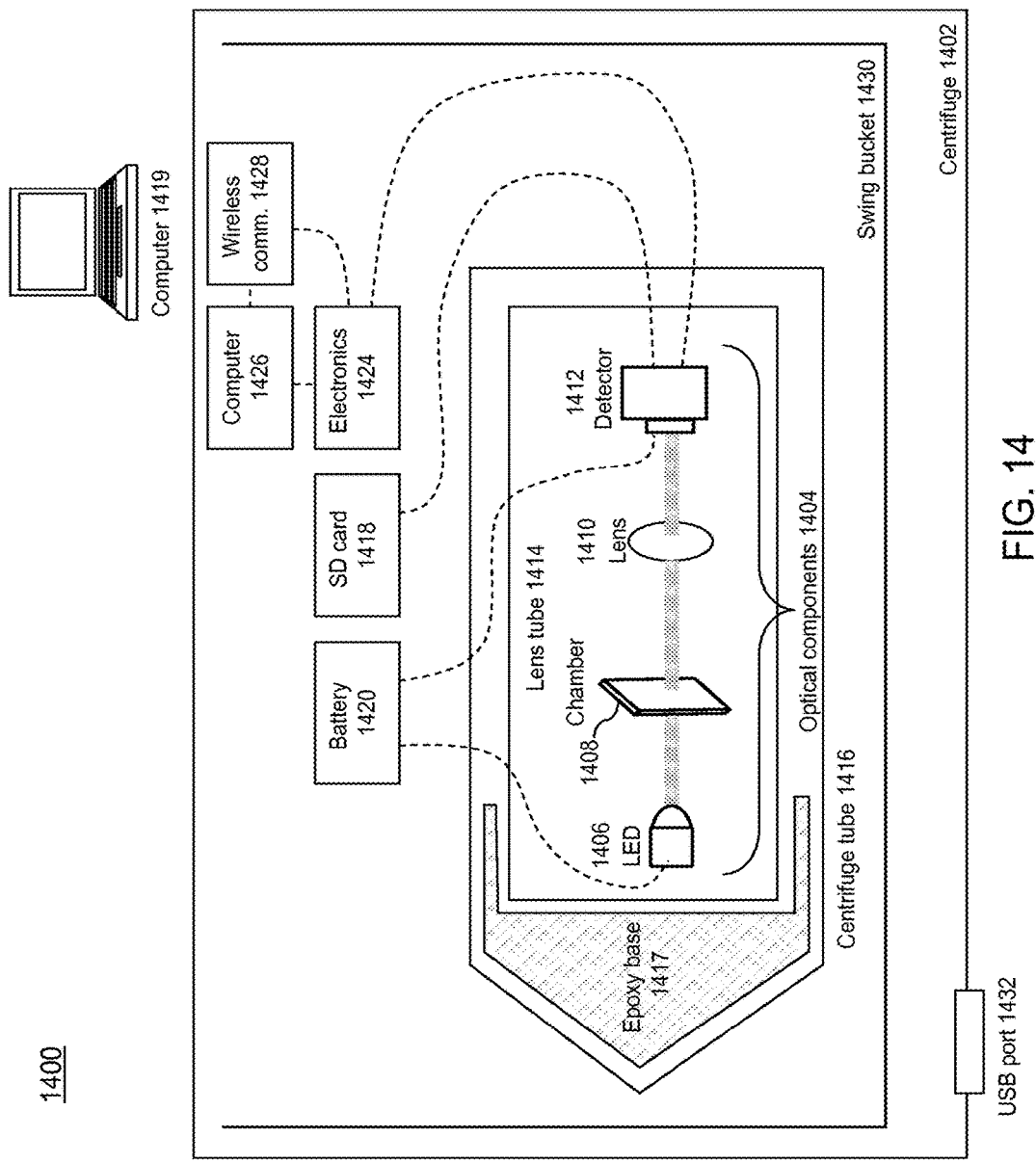
FIG. 14 is a block diagram of a small-scale spinning force system.

Referring to FIG. 14, in an alternate embodiment, a small-scale spinning force system 1400 uses a standard laboratory centrifuge 1402 to provide rotational force for the study of molecular interactions. Spinning force system 1400 includes optical path components 1404, including an LED light source 1406 (e.g., an LED525E available from Thorlabs), a sample chamber 1408, a lens 1410 used for magnification, and a detector 1412, such as a consumer-grade 5 Megapixel CCD camera or a CMOS (complementary metal-oxide-silicon) camera. Detector 1412 is, for instance, a VholdR (Seattle, Wash.) Contour HD CCD camera. Lens 1410 may be an aspheric lens (such as lens C230TME-A available from Thorlabs) that is sufficiently aberration-free to allow only a single lens to be used; alternatively, lens 1401 may be a multi-lens microscope objective. In some cases, optical path components 1404 act as a roughly 10× microscope. In some embodiments, a lens is not used and the detector 1412 receives light directly from sample chamber 1408.

Optical path components 1404 are aligned within a lens tube 1414, such as a ½ inch diameter SM05 lens tube (Thorlabs), placed inside of a centrifuge receptacle. In some embodiments, the centrifuge receptacle is a standard centrifuge tube 1416, such as a plastic centrifuge tube having a volume of, e.g., 50 mL, 15 mL, 1.5 mL, or another volume. A cone-shaped base 1417 formed from molded epoxy fits snugly at the end of centrifuge tube 1416. A hole is drilled in the center of epoxy base 1417 and the LED end of the lens tube 1414 is inserted into the hole in the base 1417, stabilizing the position of the optical components 1404 within centrifuge tube 1416. In some cases, such as that shown in FIG. 14, centrifuge tube 1416 is placed within a swing bucket 1430 of centrifuge 1402; in other cases, centrifuge 1402 is configured to accept centrifuge tube 1416 in a centrifuge tube holder (not shown). In an alternate embodiment, the centrifuge receptacle is itself a standard centrifuge bucket, e.g., a bucket configured to hold multiple centrifuge tubes. In still other embodiments, the centrifuge receptacle may be a modified centrifuge rotor.

Figure 15:
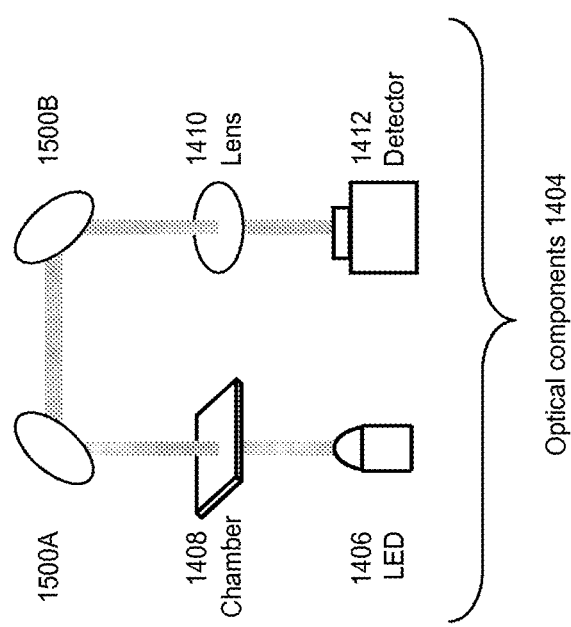
FIG. 15 is a block diagram of an alternative arrangement of optical components in a small-scale spinning force system.

Referring to FIG. 15, in an alternative embodiment, for a more compact setup, the optical path of optical path components 1404 is bent by two 45 degree mirrors 1500a, 1500b.

Referring again to FIG. 14, a memory device, such as a solid-state secure digital (SD) card 1418, records video signals received from CCD camera 1412 representative of images of the sample formed by lens 1410. The video images recorded on SD card 1418 can be analyzed by an external computer 1419 after an experiment is completed. Both camera 1412 and LED 1406 are powered by a small battery 1420, such as a lithium polymer battery. In some embodiments, SD card 1418 and battery 1420 are placed in swing bucket 1430 along with centrifuge tube 1416, with electrical connections between SD card 1418 and camera 1412 and between battery 1420 and both LED 1406 and camera 1412. Electronic components 1424 (e.g., a circuit board) that control camera 1412 are also positioned in swing bucket 1430. In this configuration, SD card 1418, battery 1420, and electronic components 1424 rotate along with the optical path components 1404, but are not subject to size constraints that would be imposed by assembly within centrifuge tube 1416. In other embodiments, SD card 1418, battery 1420, and electronic components 1424 are placed in another centrifuge tube (not shown), which may be positioned within the swing bucket 1430 along with centrifuge tube 1416, or which may be placed in another centrifuge tube holder. In still other embodiments, SD card 1418, battery 1420, and electronic components 1424 are small enough to be positioned within centrifuge tube 1416. A port 1432, such as a Universal Series Bus (USB) port, is included in centrifuge 1402 to enable computer control of the rotation.

In some embodiments, an onboard computer 1426 (e.g., a small computer available from gumstix, Portola Valley, Calif.) is placed in the centrifuge tube 1416 or in the modified swing bucket 1422. The onboard computer is capable of locally analyzing the video received from CCD camera 1412; the results of the analysis are stored on SD card 1418. In other embodiments, a wireless communication device 1428 is used in addition to or in place of SD card 1418 so that the video feed from the detector can be transmitted in real time and analyzed with a remote computer. Alternatively, the wireless communication device communicates with the onboard computer such that analyzed results can be transmitted in real time.

Figure 16:
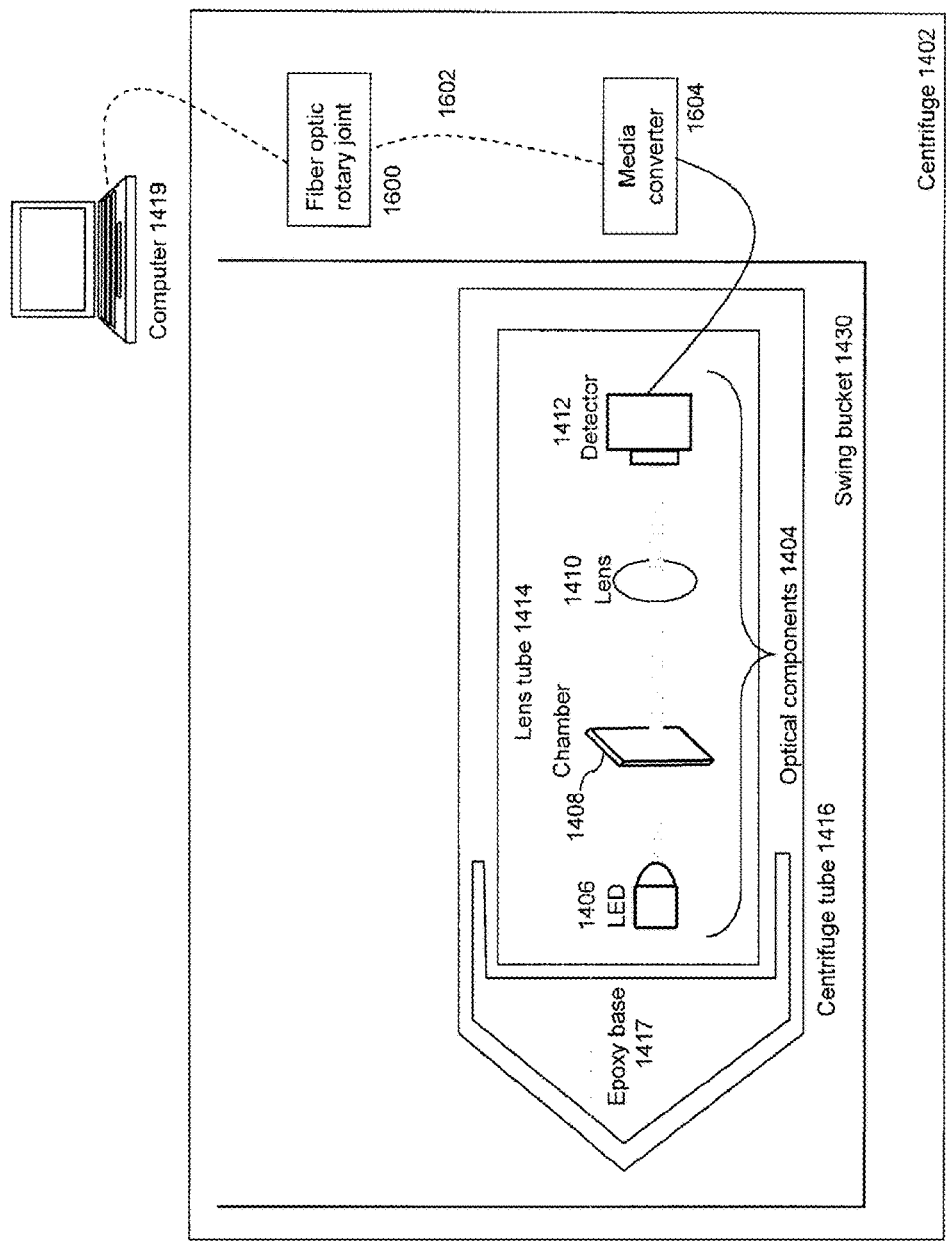
FIG. 16 is a block diagram of an alternative embodiment of a small-scale spinning force system.

Referring to FIG. 16, in still other embodiments, a fiber optic rotary joint 1600 integrated into centrifuge 1402 enables high speed communications between the standard laboratory environment (i.e., computer 1419) and the rotating sample. Data is transmitted from detector 1412 to an Ethernet-to-fiber media converter 1604 and then to external computer 1419 via fiber optic cable 1602 passing through fiber optic rotary joint 1600. Power for the electronic components in centrifuge tube 1416 may also be transmitted in a similar fashion, allowing dynamic control of these components during rotation of the small-scale system.

The principle of operation of small-scale spinning force system 1400 is similar to the operating principle of the spinning force system 100 described above. In spinning force system 1400, sample chamber 1408 is loaded with functionalized microspheres (e.g., 3 µm latex beads coated with molecule "A") and a functionalized cover slip (e.g., a glass cover slip coated with molecule "B"). The "A"-functionalized beads are brought into contact with the "B"-functionalized cover slip for a short time, for instance by turning centrifuge tube 1416 upside down. The lens tube 1414 and other components, such as SD card 1418, battery 1420, and electronic components 1424, are secured within centrifuge tube 1416 and/or swing bucket 1422. CCD camera 1412 is enabled such that video recording to the SD card 1418 is initiated. The centrifuge is properly balanced, if necessary, and rotation is started. Once the centrifuge is spinning, the "A"-functionalized particles will experience a force away from the "B"-functionalized cover slip. As described above, some particles bound to the cover slip via A-B molecular complexes will separate from the cover slip at various times; this time signature reveals the force-dependent dissociation of the A-B complex. Video analysis of the resulting data is performed after centrifugation is completed using particle detection techniques described herein.

4 Applications

Using the centrifugal force (and possibly other forces) of a spinning sample, spinning force system 100 is capable of performing single-molecule experiments for application in a wide range of areas, including receptor-ligand interactions, DNA mechanics, the kinetics of motor proteins, and the dynamics of intramolecular transitions such as protein folding and unfolding. In addition, spinning force system 100 can also be used for high-throughput molecular screening in which thousands of single-molecule experiments of the same or different types can be performed in parallel and/or in series. This can be particularly useful for drug discovery and screening The following section provides several scenarios in which spinning force system 100 is useful.

4.1 Example I

One application of spinning force system 100 relates to studying the molecular interactions between two or more interacting molecules or molecular complexes, including, for example, measuring the association rate $K_{on}$ and dissociation rate $K_{off}$ of the interaction, identifying metastable states, and determining the transition rates between such states. Examples of interacting molecules suitable as subject of study include receptor-ligand pairs, such as biotin-streptavidin, antibody-antigen, enzyme-substrate, and DNA-polymerase.

Referring to FIGS. 5A-5D, one procedure of preparing a sample containing two interacting molecules A (e.g., biotin) and B (e.g., streptavidin) for measurement is illustrated.

Figure 5A:
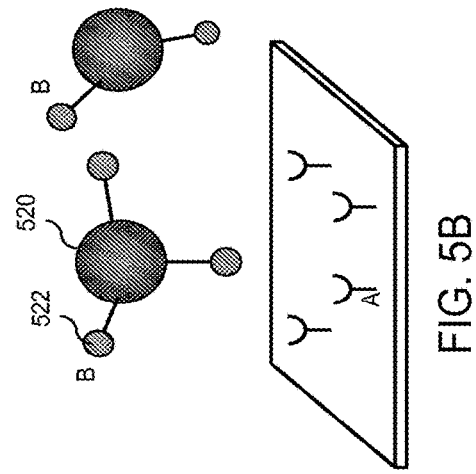
FIGS. 5A-5D are schematic representations of a procedure for preparing a sample to be measured by the spinning force system of FIG. 1.

For example, in FIG. 5A, a cover glass 510 is coated with a dispersed layer of molecule A 512 using proper functionalization techniques such as physisorption or covalent linkage.

Figure 5B:
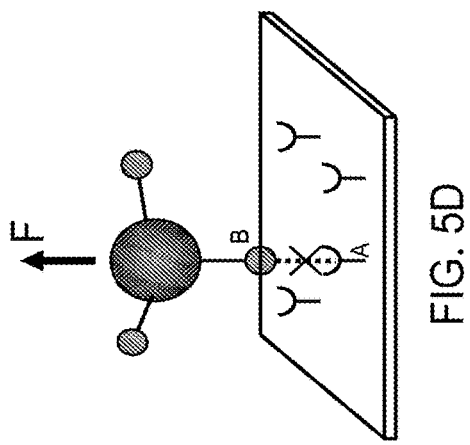

In FIG. 5B, a solution of glass beads 520 is then added onto cover glass 510. Each bead is pre-coated with one or more molecules B 522, again using proper functionalization techniques.

Figure 5C:
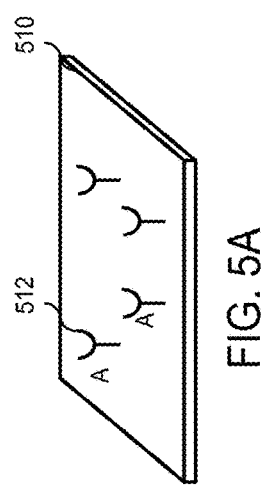

In FIG. 5C, cover glass 510 is incubated with glass beads 520 to enable formation of interaction 530 between molecules A and B. Consequently, some beads 520 become attached to the surface of cover glass 510 through newly formed interactions 530. Unattached beads can be removed from the surface by rinsing with an inactive solution, or alternatively, removed by a centrifugal force applied during measurement. In some examples, the amount of interactions 530 formed during the incubation can be controlled, for example, by the temperature and time duration of the incubation, the concentration of pre-coated bead solution, and the density of molecule A 512 seeded on cover glass 510.

Figure 5D:
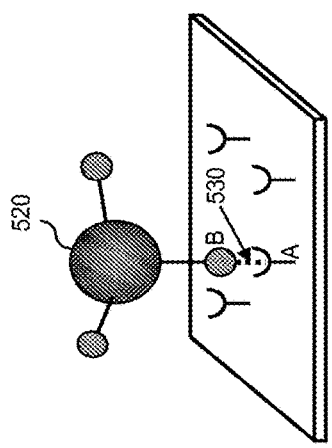

In FIG. 5D, once the sample is ready for measurement, it is loaded onto spinning force system 100. In this example, cover glass 510 is configured to be parallel to rotational axis 102 of system 100. The rotation of the sample therefore results in a centrifugal force F on bead 520, pulling it away in a direction perpendicular to the surface of cover glass 510. The movement of bead 520 can be monitored using one or more of the imaging techniques described above. When the magnitude of centrifugal force F is sufficiently high to rupture interaction 530, bead 520 is released from cover glass 510.

In this example, hundreds or thousands of molecular interactions 530 can be formed and observed in one experiment, allowing statistical analysis of such observations to be performed in a highly efficient manner.

4.2 Example II

Another application of spinning force system 100 relates to studying the intramolecular dynamics of a single molecule or a molecular tether (e.g., a protein or a DNA tether), including, for example, measuring the folding, unfolding, stretching, and relaxation of a molecular strand.

FIGS. 6A-6D illustrate use of system 100 in a procedure for preparing a sample containing a molecular tether to be measured.

Figure 6B:
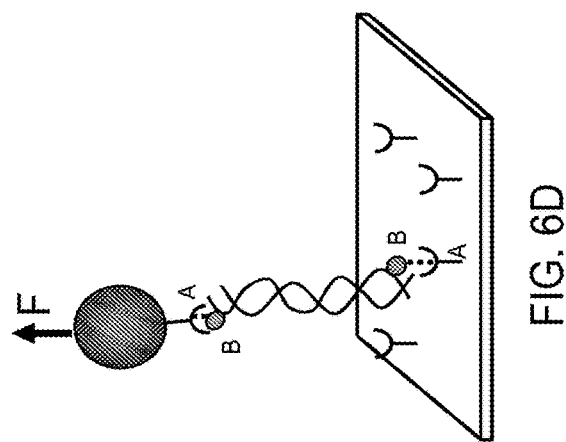
FIGS. 6A-6D are schematic representations of another procedure for preparing a sample to be measured by the spinning force system of FIG. 1.
Figure 6A:
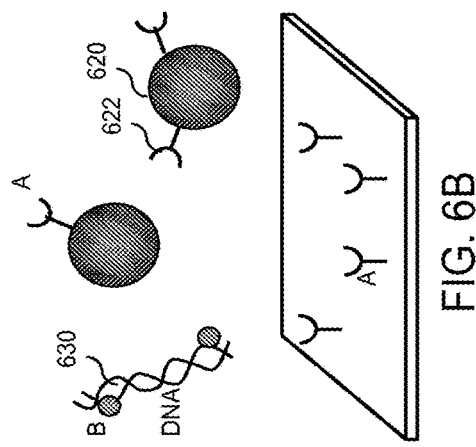

In FIG. 6A, a cover glass 610 is coated with a dispersed layer of molecule A 612 using proper functionalization techniques such as physisorption.

Figure 6D:
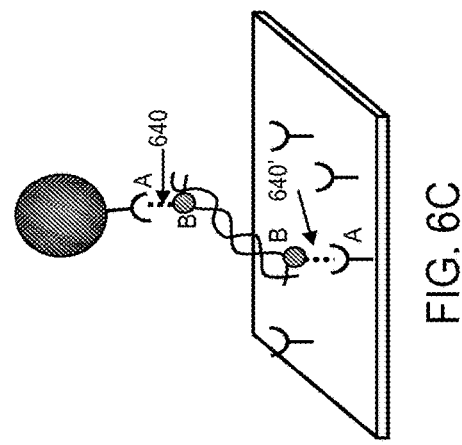
Figure 6C:
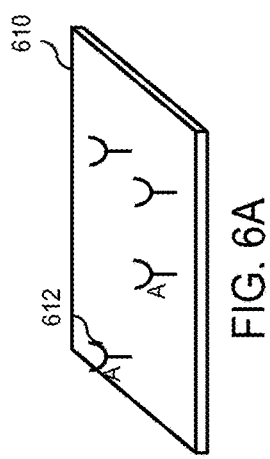

In FIG. 6B, a solution of glass beads 620 and a solution of molecular tethers 630 (e.g., DNA tethers as shown in FIGS. 6B-6D for illustrative purposes) are added onto cover glass 610. Each bead 620 is pre-coated with one or more molecule A 612, and each molecular tether 630 is functionalized with one or more molecule B 632 capable of forming interactions with molecule A 612. Examples of commonly used functionalization techniques and procedures include silanization for glass substrate, formation of a peptide bond between a carboxylated surface and a free amine on a protein, and formation of disulfide bonds or S—C bonds for cysteine residues.

In FIG. 6C, cover glass 610 is incubated with glass beads 620 and molecular tether 630 to enable formation of interaction 640 between molecules A and B. Consequently, some beads 620 become attached to the surface of cover glass 610 through a newly formed interaction 640 between bead 620 and molecular tether 630 and another newly formed interaction 640' between molecular tether 630 and cover glass 610. Unattached beads can be removed from the surface by rinsing with an inactive solution, or alternatively, removed by a centrifugal force during measurement. In some examples, the amount of interactions 640 formed during incubation can be controlled, for example, by the temperature and time duration of incubation, the concentration of pre-coated bead solution and molecular tether solution, and the density of molecule A 612 seeded on cover glass 610.

In FIG. 6D, once the sample is ready for measurement, it is loaded onto spinning force system 100. For illustrative purposes, cover glass 610 is configured to be parallel to rotational axis 102 of system 100. The rotation of the sample therefore results in a centrifugal force F on bead 620, pulling it away in a direction perpendicular to the surface of cover glass 610. The movement of bead 620 indicates the force-induced conformational changes of molecular tether 630 and can be used to measure variables characterizing the folding, unfolding, stretching and relaxation of the molecular tether in response to an external force. When the magnitude of F is varied (without exceeding the bond rupture force to break interaction 634), the force dependent dynamics of DNAs can also be quantified.

Again, in this example, hundreds or thousands of molecular tethers 630 can be studied in a single experiment, allowing statistical analysis of the results to be performed efficiently.

4.3 Example III

Another application of spinning force system 100 relates to studying the characteristics of molecules or molecular interactions in controlled chemical environments, including, for example, quantifying molecular dynamics at various temperatures, pH conditions, and/or salt concentrations, as well as in the presence of various kinds of surfactants and/or enzymes.

FIGS. 7A-7D illustrate use of system 100 in a procedure for preparing a sample containing a molecular tether 730 that can be modified by a restriction enzyme 760.

For example, in FIG. 7A, molecular tether 730 (e.g., a DNA strand) is attached to a cover glass 710 and a particle 720 using preparation techniques described above with reference to FIGS. 6A-6C.

In FIG. 7B, a solution of restriction enzymes 760 is added onto cover glass 710. Examples of restriction enzyme 760 include an enzyme that cuts double-stranded or single-stranded DNA at specific recognition nucleotide sequences (known as restriction sites). Restriction enzymes can be used for manipulating DNA in various applications such as DNA digestion and gene insertion.

In FIG. 7C, molecular tether 730 is incubated in the solution of restriction enzymes 760 to allow one or more enzyme molecules to bind to the restriction sites of tether 730.

In FIG. 7D, upon binding with tether 730, restriction enzyme 760 makes incisions at selected locations in tether 730, cutting the tether into two or more disconnected pieces. As a result, particle 720 is released from the surface of cover glass 710. Particle release can be observed using the imaging techniques described above.

Some or all of the procedures shown in FIG. 7A-7D may be performed during spinning. For example, the binding/interaction between tether 730 and restriction enzyme 760 may be monitored under the influence of a controlled centrifugal force applied to particle 720 as shown in FIG. 6D.

4.4 Example IV

Referring to FIGS. 11A-11D, in a specific example, spinning force system 100 is used to perform massively parallel single-molecule experiments for the characterization of the force-dependent unbinding kinetics of an antibody-antigen interaction.

Referring to FIG. 11A, a cover glass 1110 is coated with a dispersed layer of digoxigenin (molecule A 1112). Functionalized cover glass 1110 was prepared by base washing a glass coverslip (immersed for 5 minutes in a boiling solution of 1 part 30% $H_2O_2$, 4 parts $NH_4OH$, and 19 parts $d-H_2O$), followed by adsorption of monoclonal anti-digoxigenin (11094400, mouse monoclonal, available from Roche, Boulder, Colo.). The cover glass was then washed with a blocking buffer composed of phosphate buffered saline with 0.1% Tween 20 and 1 mg/mL dephosphorylated alpha-casein (C8032, Sigma Aldrich, St. Louis, Mo.). The experiments described below were performed in the same blocking buffer to decrease non-specific adhesion of beads to the surface of cover glass 1110.

In FIG. 11B, digoxigenin (molecule B 1132) was tethered to glass beads 1120 with a diameter of 2.8 microns by molecular tethers, e.g., DNA tethers 1130. Monoclonal anti-digoxigenin (molecule A 1112) is capable of forming a bond with digoxigenin (molecule B 1132). More specifically, diogoxigenin labeled DNA was prepared by labeling the cohesive ends of 48 kB lambda phage DNA (N3013S, available from New England Biolabs, Ipswich, Mass.) with biotin (biotin-14-dATP and biotin-14-dCPT, available from Invitrogen) using Klenow polymerase (M0212S, available from New England Biolabs), follows by purification using, for instance, QiaQuick purification kit available from Qiagen (Valencia, Calif.). The biotinylated DNA was then cut in half with the Xbal restriction enzyme (R014SS, New England Biolabs) and re-purified. The overhanging ends of the resulting 24 kB DNA were filled in and labeled with a single digoxigenin (dig-11-dUTP, available from Roche) or plain nucleotides for dig-labeled or unlabeled DNA. Finally, the DNA was re-purified and the dig-DNA was mixed with unlabeled DNA in a 1:4 ratio. The mixture of dig-DNA and unlabeled DNA was reacted with streptavidin labeled beads (Dynabeads M-270, available from Invitrogen, Carlsbad, Calif.) for use in the experiment.

In FIG. 11C, cover glass 1110 is incubated with a solution of the DNA-functionalized glass beads 1120 to enable the formation of bonds between molecules A and B. Consequently, some beads 1120 (e.g., beads 1 and 2) become attached to the surface of cover glass 1110 through a newly formed bond between molecules A on cover glass 1110 and molecules B attached to beads 1 and 2. Other beads, such as bead 3, are non-specifically bound to the surface of cover glass 1110, for instance by hydrogen bonding. In some examples, the amount of bonds formed during incubation can be controlled, for example, by the temperature and time duration of incubation, the concentration of pre-coated bead solution, and the density of molecule A 1112 seeded on cover glass 1110.

In FIG. 11D, once the sample is ready for measurement, it is loaded onto spinning force system 100 and rotated at a constant velocity in order to apply a uniform force field to all of the beads in a direction perpendicular to the surface of cover glass 1110. Some singly-tethered beads (e.g., bead 1) responded by moving away from cover glass 1110 by a distance x consistent with the compliance of the double-stranded DNA tether 1130. Other singly-tethered beads (e.g., bead 2) detached from cover glass 1110 as a result of the rupture of the bond between molecules A and B. Non-specifically bound beads (e.g., bead 3) remained at or near the surface of cover glass 1110.

Figures 12A, 12B, 12C, 12D:
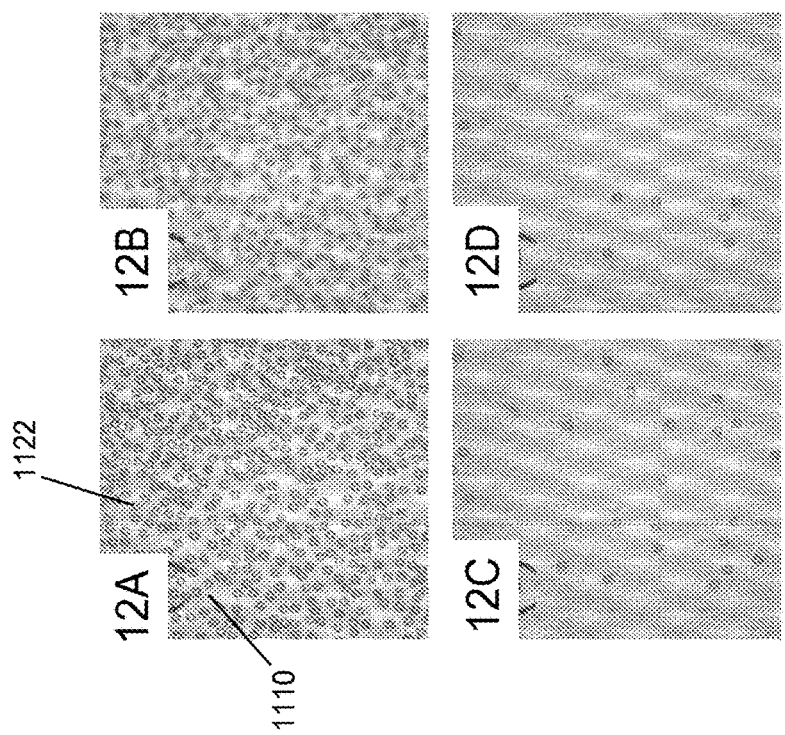
FIGS. 12A-12D are images of a spinning force experiment using the sample of FIGS. 11A-11D.

Referring to FIGS. 12A-12D, time lapse images show the progress of the bond rupture experiment illustrated in FIG. 11D. The images are obtained from videos recorded at 10 frames per second. At the start of the experiment (FIG. 12A), thousands of anti-digoxigenin functionalized beads 1122 are bound to cover glass 1110. Prior to beginning the experiment, the objective lens (150 in FIG. 1) of spinning force system 100 is focused at a distance of one tether-length (x) away from the surface of cover glass 1110 (FIG. 12B). Since all the beads are resting on the surface of the cover glass at the start of the experiment, the beads are not in the focal plane of the objective lens and thus appear blurry. When a centrifugal force is generated that pulls the beads away from cover glass 1110, beads tethered by a single DNA molecule move into focus (FIG. 12C). As single receptor-ligand bonds (i.e., digoxigenin—anti-digoxigenin bonds) rupture, beads detach from cover glass 1110, resulting in fewer visible beads over time (FIG. 12D).

Force clamps ranging from hundreds of femtoNewtons to several picoNewtons were applied using spinning force system 100. Analysis of videos of the experiment was performed by identifying locations of fully tethered beads at a frame near the beginning of the movie (once full rotational speed was reached) and analyzing small regions of interest at each location in subsequent frames to determine the time of bond rupture. Bead locations were determined by performing a background subtraction, making a binary image, and finding the center positions and the variance of a region of interest around each bead. The image variance is important because non-specifically adsorbed ("stuck") beads can be distinguished from tethered beads by their variance. Stuck beads were excluded from the analysis. The rupture time for each bead was identified by a dramatic drop in the measured variance to near zero, corresponding to a grey, bead-free image. In rare cases, where multiple drops in the variance were observed for a particular bead, that bead was excluded form analysis, as this behavior indicated the possibility of a multiple tether.

Figure 13:
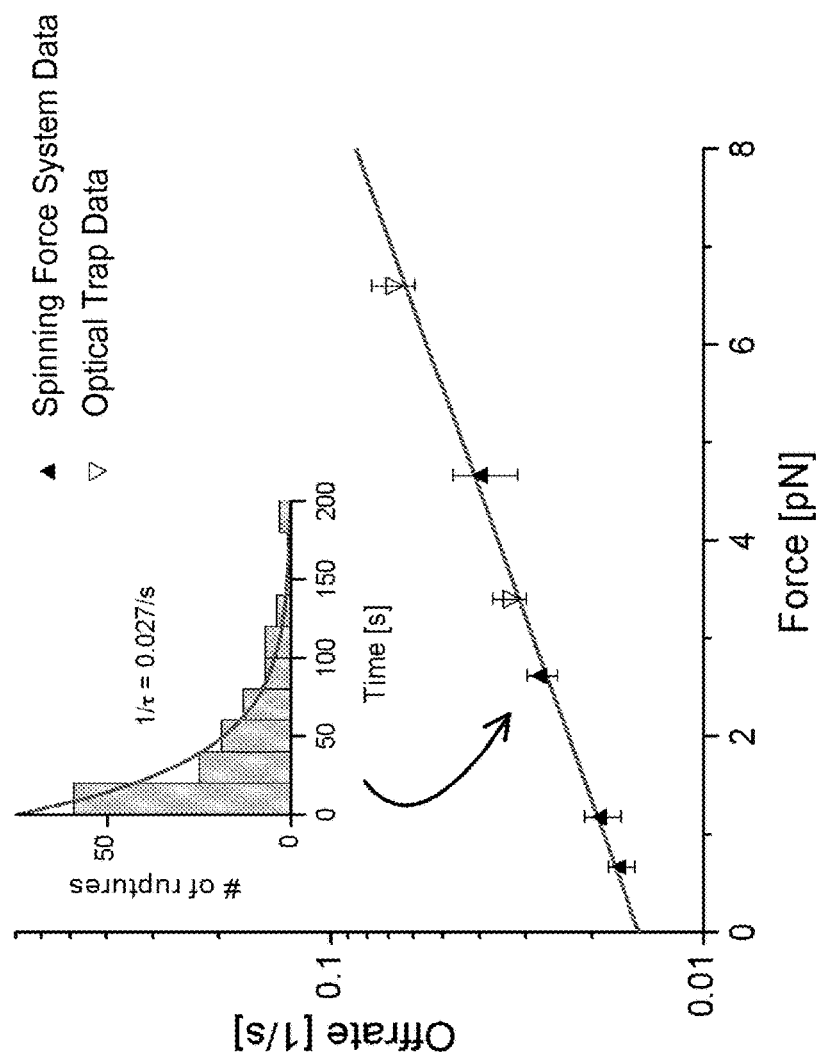
FIG. 13 is a graph of data collected during the experiment of FIGS. 12A-12D.

Referring to FIG. 13, a histogram of the bond rupture time obtained using spinning force system 100, with a 20 second bin width (10 seconds for the highest optical trap force), was fit with a decaying exponential curve with no offset. The resulting time constants and associated fitting errors were used to determine the force-dependent off-rate $k_{off}(f)=k_0 \exp(f/f_\beta)$ for the interaction of digoxigenin and its antibody using an Arrhenius approach with force-dependence modeled by a single, sharp barrier.

The force imparted on the beads by spinning force system 100 was calculated as $F=m\omega^2 R$, where $m=6.9\times10^{-12}$ g is the mass of the bead (calculated using the manufacturer's bead specifications of 2.8 mm diameter and 1.6 g/cm$^3$ density), R=385.5 mm is the distance of the bead from the axis of rotation, and $\omega$ is the magnitude of the angular velocity of the system. A small additional force from the weight of the bead was included using the Pythagorean theorem. The data plotted in FIG. 13B includes data obtained using spinning force system 100 (filled triangles) and using an optical trap system (open triangles). Each spinning force system data point was obtained from a single experiment lasting a few minutes. Plotted error bars result from the uncertainty in a least squares fit to the data. A stress-free off-rate of $k_0=0.015\pm0.002$ s$^{-1}$ and a force scale of $f_\beta=4.6\pm1.3$ pN were found. These results are in good agreement with previously determined optical trap data and fall within the margin of error of previous AFM experiments.

4.5 Example V

Another application of spinning force system 100 relates to studying different types of molecular interactions and/or molecular dynamics in parallel. This application allows a direct comparison of molecular events of similar or different nature, such as the mobility of two different motor proteins, the compliance of various pieces of DNA strands, and the affinity of various receptor-ligand pairs. To distinguish the observations of motion characteristics resulted from distinct molecular events, each type of event can be uniquely labeled, for example, using fluorescent tracers or other kinds of markers. For example, in cases where two types of cytoskeletal proteins (e.g., microtubules and actin filaments) are studied at once, each type can be labeled by fluorescent beads of distinct emission wavelengths. By using selected optical filters to alternate observation of photons of different colors, the motion characteristics of each type of cytoskeletal proteins can be distinguished based on the resulting fluorescent images.

4.6 Example VI

Although the previous examples are provided primarily in the context of measuring molecular dynamics or interactions, spinning force system 100 is also useful in measuring characteristics of interactions that occur on a cellular and/or tissue level. One example is to study the adhesion strength between adherent cells (e.g., endothelial or epithelial cells) and the underlying substrate or matrix to which the cells adhere. A monolayer of adherent cells can be seeded on a receptor-modified (e.g., fibronectin-coated) cover glass to form adhesion complexes (e.g., clusters of adhesion molecules such as integrins, syndecans, and cadherins). The cover glass is then mounted to rotary arm 120 and cells are monitored during rotation. The magnitude of centrifugal force that detaches cells from the cover glass indicates the maximum adhesion strength of the adhesion complexes.

4.7 Example VII

Another application of spinning force system 100 relates to using system 100 in conjunction with other detection or measurement techniques (e.g., various kinds of single-molecule force probes or fluidic systems) to obtain force-related characteristics of the sample. For example, system 100 can be combined with a magnetic system to apply both magnetic and centrifugal forces to manipulate a test subject. A biotin labeled magnetic bead can be first pulled by a magnetic force toward a cell membrane (or a streptavidin-treated surface) to form a biotin-streptavidin attachment. The strength of this attachment can then be tested by applying a centrifugal force that pulls the bead away from the membrane.

System 100 can also be combined in use with devices that apply various types of chemical stimuli (e.g., chemoattractants and enzymes) and mechanical stimuli (e.g., compression, extension, and shearing) to a test subject, simulating the native environment of the subject during observation. For example, when system 100 is used for measuring the mechanical properties (e.g., elasticity or viscoelasticity) of endothelial cells, during spinning, a laminar or cyclic shear stress may also be provided to mimic the conditions of the endothelial cells in vivo. Additionally, cellular response to chemical/mechanical stimuli may also be observed.

4.8 Other Examples

In addition to detecting characteristics of biomolecular or chemical interactions, system 100 is also suitable for use with a wide range of general testing tasks. Examples include 1) measuring the mechanical properties of polymer networks or aggregates, where the overall behavior of the network may be of interest; 2) testing the strength and other characteristics of physical bonds formed between a subject and a surface; and 3) observing the behavioral changes of test subjects effected by chemical agents (e.g., an enzyme slicing a single DNA between two surfaces or urea denaturing a protein).

The use of a fiber optic rotary joint with small-scale system 1400 is generally useful for communicating with rotating samples, for instance for applications related to monitoring blood sorting.

5 Alternative Embodiments

Many variations of spinning force system 100 are possible.

Figure 8:
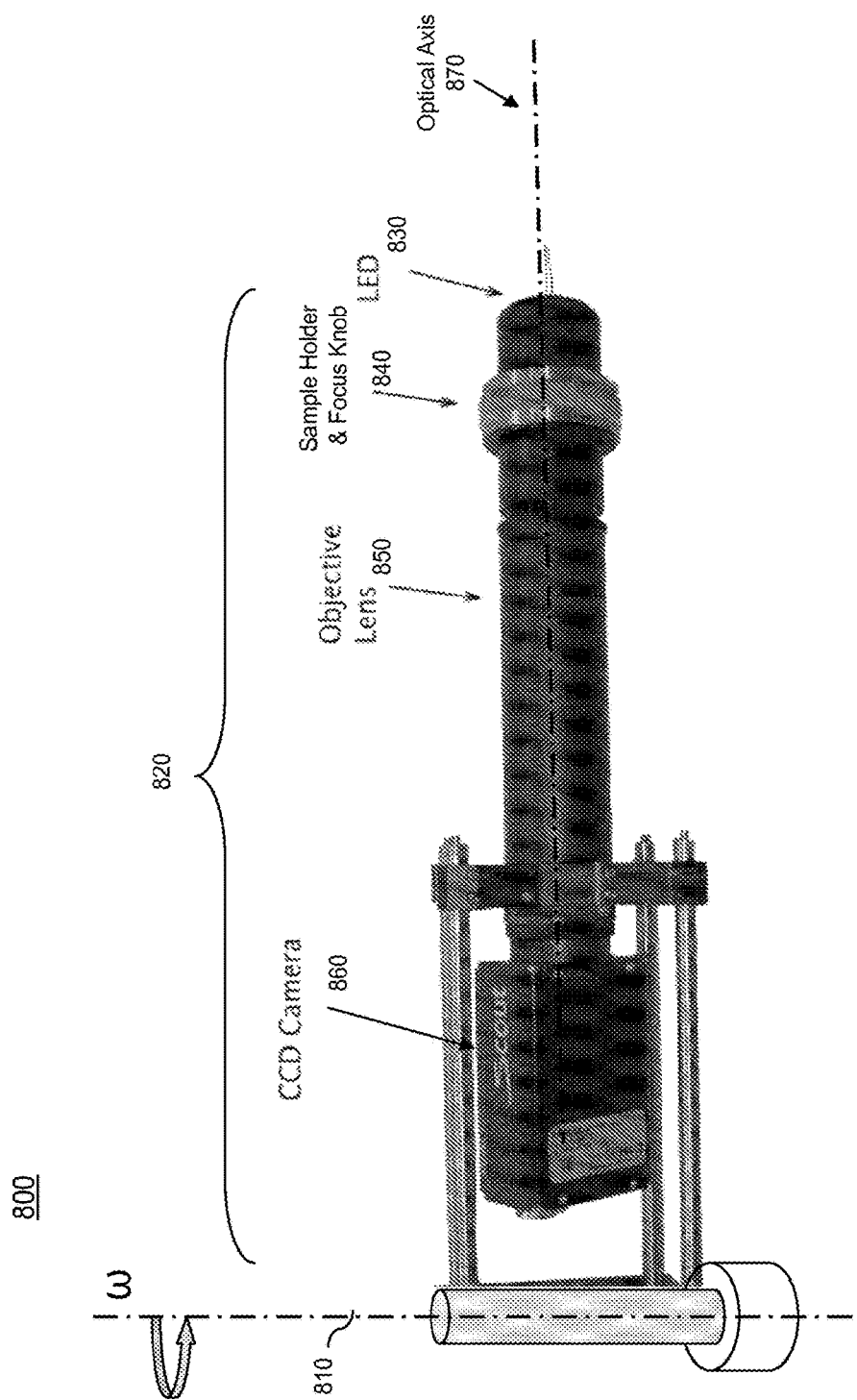
FIG. 8 shows an alternative embodiment (schematic in part) of the spinning force system of FIG. 1.

Referring to FIG. 8, an alternative embodiment of spinning force system 800 includes a coaxial detection assembly 820 mechanically coupled to a rotary stage 810. Detection assembly 820 includes a LED lamp 830, a sample holder 840, an objective lens 850, and a CCD camera 860, each being coaxially aligned with optical axis 870. LED lamp 830 is integrated into sample holder 840, which can be translated (e.g., along optical axis 870) through a focus knob for coarse adjustment. Fine adjustment of the position of sample holder 840 can be performed using a piezoelectric stage coupled to the holder (not shown). When rotary stage 810 operates in circular motion at angular velocity ω, the entire detection assembly 820 rotates at ω.

In some implementations, detection assembly 820 may be miniaturized to fit inside a standard centrifuge, eliminating the need for rotary stage 810 and reducing system cost.

Figure 9:
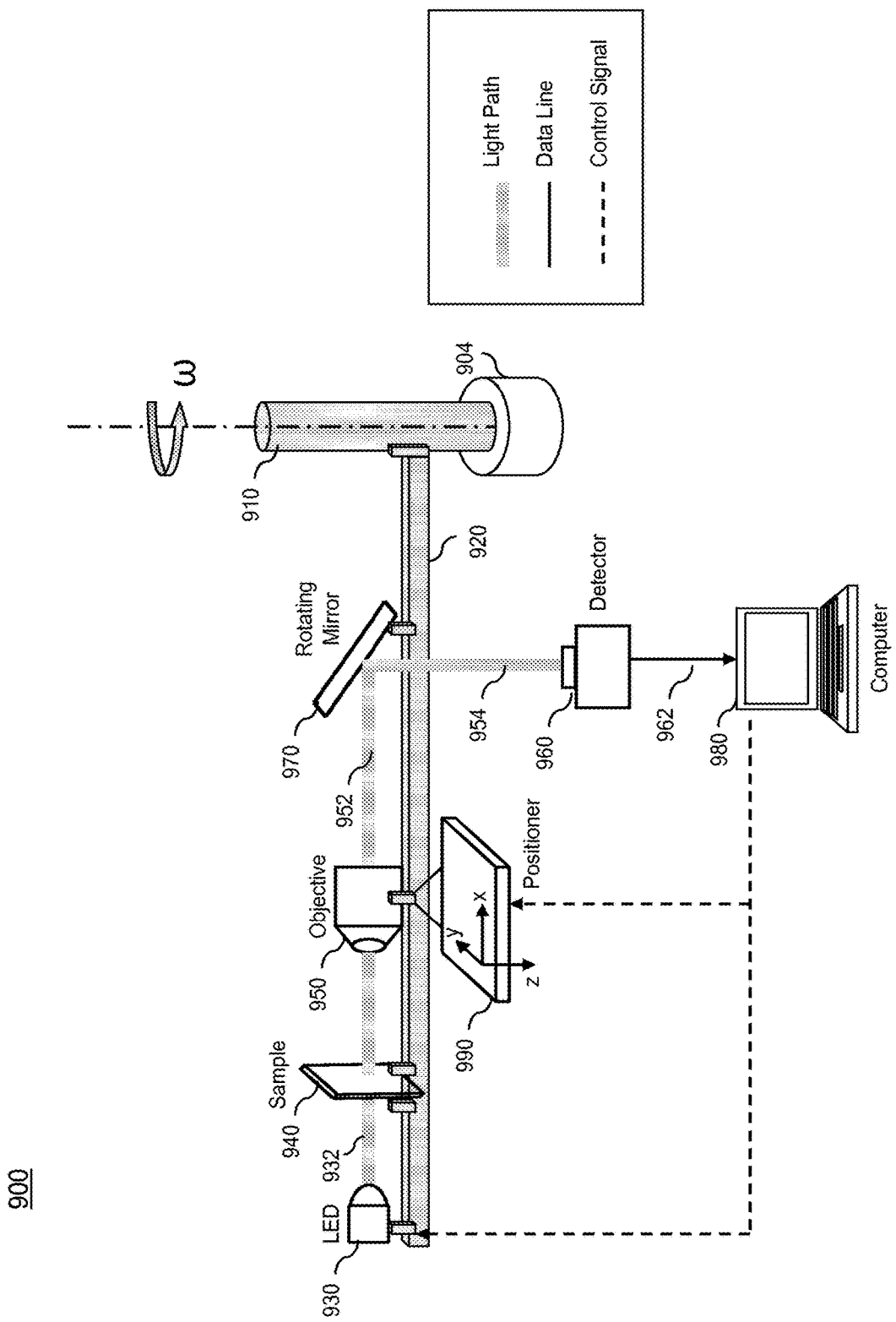
FIG. 9 shows an additional alternative embodiment of the spinning force system of FIG. 1.

Referring to FIG. 9, another alternative embodiment of spinning force system 900 is shown. Unlike detector 160 in system 100, detector 960 in this example is not mounted on rotary arm 920. Rather, detector 960 remains immobile during operation of system 900. Light from objective 950 are directed by a rotating mirror 970 to detector 960 through light paths 952 and 954 subsequently. Rotating mirror 970 is not necessarily mounted on rotary arm 920. For example, mirror 970 can be coupled to a separate rotor (not shown) or directly coupled to rotary stage 910 in order to reflect light from the rotating objective 950 to the stationary detector 960.

In the above examples of FIGS. 1, 8, and 9, the samples are detected using trans-illumination imaging techniques. More specifically, in FIG. 1, light 132 emitted from LED 130 transmits (penetrates) through sample 140 prior to being received by objective 150. In other examples, cpi-illumination imaging techniques can also be conveniently used.

Figure 10:
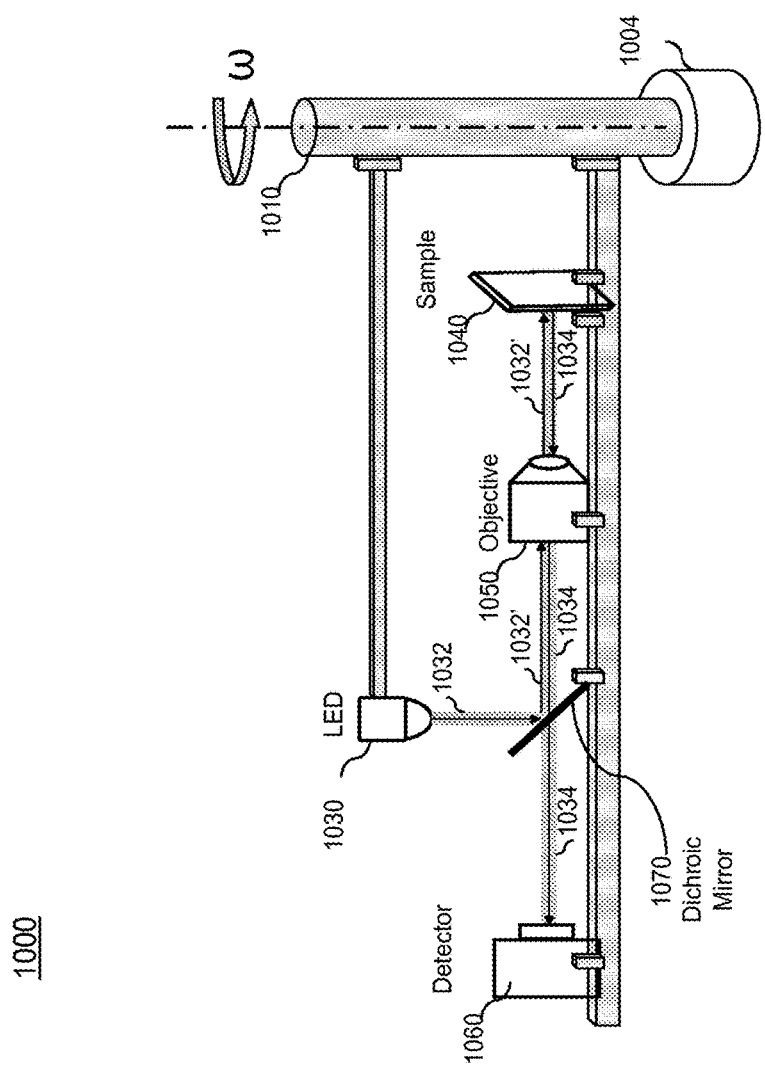
FIG. 10 shows a further alternative embodiment of the spinning force system of FIG. 1.

Referring to FIG. 10, a further alternative embodiment of spinning force system 1000 with epi-illumination is shown. Here, a Dichroic mirror 1070 is positioned between detector 1060 and objective 1050, serving as a beam splitter that directs light beams of different characteristics (e.g., different wavelengths) onto different paths. For example, light beam 1032 from LED 1030 is first deflected by Dichroic mirror 1070 towards objective 1050 (along light path 1032') to illuminate a selected region of sample 1040. A light beam 1034 is reflected from sample 1040 as a result of the illumination, travelling in a direction opposite to light beam 1032'. After passing through objective 1050 and Dicroic Mirror 1070, light beam 1034 is received by detector 1060 to produce an image of the illuminated region of sample 1040. In this example, objective 1050 serves as both a light condenser and an imaging lens.

In some embodiments, a vertical swinging or radially movable arm may be integrated to system 100 to enhance the flexibility of force control. System 100 may also be multiplexed to have many arms, each configured to carry a unique experiment. Each arm may also have a different and possibly adjustable length to facilitate force control.

In another embodiment, the samples are detected using surface plasmon resonance techniques. For instance, referring to the example of FIGS. 5A-5D, a baseline surface plasmon resonance signal is detected for the initial configuration of FIG. 5A, in which only molecules A 512 are present on the surface of the sample. As glass beads 520 are attached to the surface of the sample via interactions between molecules A 512 and B 522, the surface plasmon resonance signal increases. When the sample is rotated in spinning force system 100, a centrifugal force F is applied to bead 520. The rupture of interaction 530, which releases bead 520 from the surface of the sample, causes a decrease in the surface plasmon resonance signal. The detection of the surface plasmon resonance allows for the study of properties such as the binding constant between molecule A and molecule B.

It is to be understood that the foregoing description is intended to illustrate and not to limit the scope of the invention, which is defined by the scope of the appended claims. Other embodiments are within the scope of the following claims.

What is claimed is:

1. An apparatus for measuring a characteristic of a sample, the apparatus comprising:
 a sample measurement apparatus, comprising:
  a light source configured to illuminate the sample; and
  a detector configured to receive light from the light source, the light source and the detector being physically arranged such that light from the light source is received by the detector after illuminating the sample,
 the sample measurement apparatus being configured to retain a sample chamber having the sample to prevent relative movement between the sample chamber and the detector during centrifugation of the sample measurement apparatus by a centrifuge,
 wherein the sample measurement apparatus is configured to be removably received within a sample holding portion of the centrifuge, the sample measurement apparatus being distinct from the sample holding portion of the centrifuge.

2. The apparatus of claim 1, wherein the sample measurement apparatus further comprises a lens configured to receive light from the sample, and wherein the detector is configured to receive light passing through_the lens.

3. The apparatus of claim 2, wherein the lens includes an aspheric lens.

4. The apparatus of claim 2, wherein the sample measurement apparatus includes only one lens.

5. The apparatus of claim 1, further comprising a centrifuge receptacle configured to receive the sample measurement apparatus.

6. The apparatus of claim 5, further comprising a base disposed within the centrifuge receptacle and configured to receive the sample measurement apparatus.

7. The apparatus of claim 5, wherein the centrifuge receptacle includes at least one of a centrifuge tube, a swing bucket, and a rotor.

8. The apparatus of claim 5, wherein the centrifuge receptacle is a centrifuge tube having a volume of less than or equal to about 50 mL.

9. The apparatus of claim 2, wherein the sample measurement apparatus further includes a lens tube, wherein the light source, the lens, and the detector are disposed within the lens tube.

10. The apparatus of claim 5, further comprising a battery coupled to the centrifuge receptacle and electrically connected to the light source and the detector.

11. The apparatus of claim 10, wherein the battery is disposed within the centrifuge receptacle.

12. The apparatus of claim 5, further comprising a recording device coupled to the centrifuge receptacle, the recording device configured to record a signal received from the detector.

13. The apparatus of claim 12, wherein the recording device is disposed within the centrifuge receptacle.

14. The apparatus of claim 1, further comprising a wireless communications module configured to wirelessly transmit a signal received from the detector.

15. The apparatus of claim 1, further comprising a computing device electrically connected to the detector.

16. The apparatus of claim 15, wherein the detector is electrically connected to the computing device via a rotary joint.

17. The apparatus of claim 5, further comprising a computing device external to the centrifuge receptacle.

18. The apparatus of claim 17, wherein the detector is optically connected to the computing device via a fiber optic rotary joint.

19. The apparatus of claim 5, wherein an optical axis of the sample measurement apparatus is substantially perpendicular to an axis of rotation of the centrifuge receptacle.

20. The apparatus of claim 1, wherein the sample measurement apparatus further comprises a first mirror configured to reflect light from the light source toward the detector.

21. The apparatus of claim 20, further comprising a second mirror that reflects light from the light source toward the first mirror.

22. The apparatus of claim 20, wherein the sample measurement apparatus comprises a U-shaped assembly having a first leg and a second leg, the light source being positioned at the first leg and the detector being positioned at the second leg.

23. The apparatus of claim 20, further comprising a centrifuge receptacle configured to receive the sample measurement apparatus.

* * * * *